United States Patent
Myers et al.

(10) Patent No.: US 11,490,623 B2
(45) Date of Patent: **\*Nov. 8, 2022**

(54) ORAL CARE COMPOSITIONS AND METHODS FOR ANTI-ATTACHMENT POLYMERS AND COATINGS

(71) Applicants: Colgate-Palmolive Company, New York, NY (US); The Trustees of the University of Pennsylvania, Philadelphia, PA (US)

(72) Inventors: Carl Myers, Wayne, NJ (US); Carlo Daep, Brooklyn, NY (US); Lynette Zaidel, Cranford, NJ (US); James Masters, Ringoes, NJ (US); Russell Composto, Philadelphia, PA (US); Hyun-Su Lee, Paoli, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/846,770

(22) Filed: Apr. 13, 2020

(65) Prior Publication Data
US 2020/0236945 A1    Jul. 30, 2020

Related U.S. Application Data

(63) Continuation of application No. 15/788,852, filed on Oct. 20, 2017, now Pat. No. 10,653,149.
(Continued)

(51) Int. Cl.
*A01N 47/44* (2006.01)
*C11D 3/37* (2006.01)
(Continued)

(52) U.S. Cl.
CPC ............ *A01N 47/44* (2013.01); *A01N 25/08* (2013.01); *A61K 8/817* (2013.01); *A61K 8/91* (2013.01);
(Continued)

(58) Field of Classification Search
None
See application file for complete search history.

(56) References Cited

U.S. PATENT DOCUMENTS

5,260,385 A * 11/1993 Iio ............................ C08F 8/30
                                                      525/328.2
6,054,504 A    4/2000 Toma
(Continued)

FOREIGN PATENT DOCUMENTS

EP    0945141      4/2000
JP    S62-230806   10/1987
(Continued)

OTHER PUBLICATIONS

Jia-Hui Yu, Jin Huang, Hu-Lin Jiang, Ji-Shan Quan, Myung-Haing Cho, Chong-Su Cho. "Guanidinylated Poly(allyl amine) as a Gene Carrier." Journal of Applied Polymer Science, vol. 112, 2009, pp. 926-933. (Year: 2009).*
(Continued)

*Primary Examiner* — Isaac Shomer

(57) ABSTRACT

Antimicrobial compositions and methods for depositing or coating the antimicrobial or antibacterial compositions on a substrate to prevent microbial adhesion are provided. The antimicrobial composition may include a cationic polymer having a poly-allylamine backbone. A portion of the poly-allylamine backbone may be functionalized with at least one of a guanidine functional group and a biguanide functional group.

6 Claims, 11 Drawing Sheets

Related U.S. Application Data

(60) Provisional application No. 62/410,483, filed on Oct. 20, 2016.

(51) Int. Cl.
| | |
|---|---|
| A61K 31/785 | (2006.01) |
| A61Q 17/00 | (2006.01) |
| C11D 3/48 | (2006.01) |
| A61Q 11/00 | (2006.01) |
| C08F 126/02 | (2006.01) |
| A61K 8/91 | (2006.01) |
| A01N 25/08 | (2006.01) |
| A61K 8/81 | (2006.01) |
| C08F 8/30 | (2006.01) |
| C09D 5/14 | (2006.01) |
| C09D 139/00 | (2006.01) |

(52) U.S. Cl.
CPC ............ *A61K 31/785* (2013.01); *A61Q 11/00* (2013.01); *A61Q 17/005* (2013.01); *C08F 8/30* (2013.01); *C08F 126/02* (2013.01); *C09D 5/14* (2013.01); *C09D 139/00* (2013.01); *C11D 3/3769* (2013.01); *C11D 3/48* (2013.01); *A61K 2800/30* (2013.01); *A61K 2800/5426* (2013.01)

(56) References Cited

U.S. PATENT DOCUMENTS

| | | | |
|---|---|---|---|
| 6,160,069 A | 12/2000 | Nakada et al. | |
| 8,211,452 B2 | 7/2012 | Miksa et al. | |
| 8,617,523 B2 | 12/2013 | Trivedi et al. | |
| 8,758,729 B2* | 6/2014 | Nowak .................. | A61K 33/22 424/49 |
| 8,906,349 B2 | 12/2014 | Schaeffer-Korbylo et al. | |
| 9,994,691 B2 | 6/2018 | Appavoo et al. | |
| 10,653,149 B2* | 5/2020 | Myers ...................... | A61P 1/02 |
| 2011/0081392 A1 | 4/2011 | de Arruda et al. | |
| 2012/0045400 A1* | 2/2012 | Nowak .................. | A61Q 11/00 424/48 |
| 2013/0164228 A1 | 6/2013 | Jaracz et al. | |
| 2015/0071982 A1 | 3/2015 | Lee et al. | |
| 2016/0158275 A1 | 6/2016 | Holmes-Farley et al. | |

FOREIGN PATENT DOCUMENTS

| | | |
|---|---|---|
| KR | 20090080168 | 7/2009 |
| WO | 2000/056344 | 9/2000 |
| WO | 2010/134904 | 11/2010 |
| WO | 2011/109151 | 9/2011 |
| WO | 2016/050493 | 4/2016 |
| WO | 2016/164316 | 10/2016 |

OTHER PUBLICATIONS

Priyanka Sahariah, Bjarni M. Óskarsson, Martha Á. Hjálmarsdóttir, Már Másson. "Synthesis of guanidinylated chitosan with the aid of multipleprotecting groups and investigation of antibacterial activity." Carbohydrate Polymers, vol. 127 (2015), pp. 407-417. (Year: 2015).*
Zheng Cao et al. "The effect of guanidinium functionalization on the structural properties and anion affinity of polyelectrolyte multilayers." Soft Matter, vol. 12, 2016, pp. 1496-1505. (Year: 2016).*
Oleksandr Grytsai, Cyril Ronco and Rachid Benhida. "Synthetic accesses to biguanide compounds." Beilstein Journal of Organic Chemistry, vol. 17, 2021, pp. 1001-1040. (Year: 2021).*
Bromberg et al., 2007, "Poly(N-vinylguanidine): Characterization, and catalytic and bactericidal properties," Polymer 48:7490-7498.
Budhathoki-Uprety et al., 2012, "Synthesis of Guanidinium Functionalized Polycarbodiimides and Their Antibacterial Activities," ACS Macro Letters 1(3):370-374.
Cado et al., 2013, "Self-Defensive Biomaterial Coating Against Bacteria and Yeasts: Polysaccharide Multilayer Film with Embedded Antimicrobial Peptide," Advanced Functional Materials 23(38):4801-4809.
Chuang et al., 2008, "Polyelectrolyte multilayers for tunable release of antibiotics," Biomacromolecules 9(6):1660-1668.
Daep et al., 2006, "Structural characterization of peptide-mediated inhibition of Porphyromonas gingivalis biofilm formation," Infection Immunity 74(10):5756-5762.
Daep et al., 2010, "Selective substitution of amino acids limits proteolytic cleavage and improves the bioactivity of an anti-biofilm peptide that targets the periodontal pathogen, Porphyromonas gingivalis," Peptides 31(12):2173-2178.
Daep et al., 2011, "Structural dissection and in vivo effectiveness of a peptide inhibitor of Porphyromonas gingivalis adherence to *Streptococcus gordonii*," Infection Immunity 79(1):67-74.
DD Iarikov, M Kargar, A Sahari, L Russel, KT Gause, B Behkam, WA Ducker. "Antimicrobial Surfaces Using Covalently Bound Polyallylamine" Biomacromolecules, vol. 15, 2014, pp. 169-179, published Dec. 6, 2013. (Year: 2013).
Delvar et al., 2015, "Interaction of Polyelectrolytes with Salivary Pellicles on Hydroxyapatite Surfaces under Erosive Acidic Conditions," ACS Appl. Mater. Interfaces 7(38):21610-21618.
Duran-Pinedo et al., 2011, "Correlation Network Analysis Applied to Complex Biofilm Communities," PLoS One 6 (12):e28438.
Gaffar et al., 1979, "Studies on antibacterially-induced staining," J. Dental Research 58:210 Abstract No. 467.
Gaffar et al., 1981, "Long-term antiplaque, anticalculus, and antigingivitis effects of benzethonium/polymer complex in beagle dogs," J. Dental Research 60(11):1897-1903.
Google Patents. English translation of WO 00056344 A1. Obtained from https://patents.google.com/patent/WO2000056344A1/en?oq=artificial+saliva on Sep. 15, 2019. Originally published in Japanese on Sep. 28, 2000, 32 printed pages. (Year: 2000).
Hannig et al., 2010, "Nanomaterials in preventive dentistry," Nat Nanotechnology 5(8):565-569.
Hidalgo et al., 2009, "Functional tomographic fluorescence imaging of pH microenvironments in microbial biofilms by use of silica nanoparticle sensors," Appl. Environ. Microbiol. 75(23):7426-7435.
Hook et al., 2001, "Variations in coupled water, viscoelastic properties, and film thickness of a Mefp-1 protein film during adsorption and cross-linking: a quartz crystal microbalance with dissipation monitoring, ellipsometry, and surface plasmon resonance study," Analytical Chemistry 73(24):5796-5804.
Illergard et al., 2011, "Bacterial-growth inhibiting properties of multilayers formed with modified polyvinylamine," Colloids and Surfaces B Biointerfaces 88(1):115-120.
International Search Report and Written Opinion in International Application No. PCT/US2017/057493, dated Dec. 12, 2017.
J Dai, DM Sullivan, ML Breuning. "Ultrathin, Layered Polyamide and Plyimide Coatings on Aluminum." Industrial Engineering Chemistry Research, vol. 39, 2000, pp. 3528-3535 (Year: 2000).
Jenkinson et al., 2005, "Oral microbial communities in sickness and in health," Trends in Microbiology 13(12):589-595.
K Iio, N Minoura. "Synthesis of Polyaffylamine Derivatives with Biguanido Groups." Journal of Polymer Science Part A: Polymer Chemistry, vol. 30, 1992, pp. 2071-2073 (Year: 1992).
Kandel et al., 2014, "Chemically grafted fibronectin for use in QCM-D cell studies," Biosens Bioelectronics 58:249-257.
Kandori et al., 2009, "Synthesis of positively charged calcium hydroxyapatite nano-crystals and their adsorption behavior of proteins," Colloids and Surfaces B Biointerfaces 73(1):140-145.
Kaplan et al., 2004, "Enzymatic detachment of *Staphylococcus epidermidis* biofilms," Antimicrobial Agents Chemotherapy 48(7):2633-2636.
Kaplan, 2010, "Biofilm dispersal: mechanisms, clinical implications, and potential therapeutic uses," J. Dental Research 89(3):205-218.
Kenawy et al., 2007, "The chemistry and applications of antimicrobial polymers: a state-of-the-art review," Biomacromolecules 8(5):1359-1384.

(56) References Cited

OTHER PUBLICATIONS

Kolenbrander, 2000, "Oral microbial communities: Biofilms, interactions, and genetic systems," Annual Review of Microbiology 54(1):413-437.
Kurt et al., 2007, "Highly effective contact antimicrobial surfaces via polymer surface modifiers," Langmuir 23(9):4719-4723.
Lee et al., 2004, "Permanent, nonleaching antibacterial surfaces. 1. Synthesis by atom transfer radical polymerization," Biomacromolecules 5(3):877-882.
Lee et al., 2008, "In Situ Study of Polymer Brushes as Selective Barriers to Diffusion," Macromolecules 41(21):8124-8129.
Lee et al., 2009, "Evidence for relative radius of gyration as the criterion for selective diffusion behavior of polymer brushes," Langmuir 25(14):7983-7989.
Lee et al., 2010, "Use of the quartz crystal microbalance to monitor ligand-induced conformational rearrangements in HIV-1 envelope protein gp120," Analytical Bioanalytical Chemistry 396(3):1143-1152.
Lee et al., 2011, "Symmetric pH-dependent swelling and antibacterial properties of chitosan brushes," Langmuir 27(20):12458-12465.
Lee et al., 2012, "Chitosan adsorption on hydroxyapatite and its role in preventing acid erosion," J. Colloid Interface Science 385(1):235-243.
Lee et al., 2012, "Reversible Swelling of Chitosan and Quaternary Ammonium Modified Chitosan Brush Layers: Effect of pH and Counter Anion Size and Functionality," J. Materials Chemistry 22(37):19605-19616.
Lee et al., 2015, "Targeted release of tobramycin from a pH-responsive grafted bilayer challenged with S. aureus," Biomacromolecules 16(2):650-659.
Lee et al., 2017, "Competitive Adsorption of Polyelectrolytes onto and into Pellicle-Coated Hydroxyapatite Investigated by QCM-D and Force Spectroscopy," ACS Appl. Mater. Interfaces 9(15):13079-13091.
Lewis et al., 2005, "Surpassing nature: rational design of sterile-surface materials," Trends in Biotechnology 23(7):343-348.
Lichter et al., 2008, "Substrata mechanical stiffness can regulate adhesion of viable bacteria," Biomacromolecules 9(6):1571-1578.
Lichter et al., 2009, "Design of Antibacterial Surfaces and Interfaces: Polyelectrolyte Multilayers as a Multifunctional Platform," Macromolecules 42(22)8573-8586.
Lichter et al., 2009, "Polyelectrolyte multilayers with intrinsic antimicrobial functionality: the importance of mobile polycations," Langmuir 25(13):7686-7694.
Lin et al., 2011, "Synthesis of element-substituted hydroxyapatite with controllablemorphology and chemical composition using calcium silicate as precursor," CrystEngComm 13:4850-4855.
Loskill et al., 2013, "Reduced adhesion of oral bacteria on hydroxyapatite by fluoride treatment," Langmuir 29(18):5528-5533.
Marsh et al., 2011, "Dental plaque biofilms: communities, conflict and control," Periodontology 2000 55(1):16-35.
Marsh, 2009, "Dental plaque as a biofilm: the significance of pH in health and caries," Compend Contin Educ Dent 30(2):76-8, 80, 83-7.
Min et al., 2014, "Tunable staged release of therapeutics from layer-by-layer coatings with clay interlayer barrier," Biomaterials 35(8):2507-2517.
Pavlukhina et al., 2010, "Polymer multilayers with pH-triggered release of antibacterial agents," Biomacromolecules 11(12):3448-3456.
Richert et al., 2004, "Layer by layer buildup of polysaccharide films: physical chemistry and cellular adhesion aspects," Langmuir 20(2):448-458.
Rickard et al., 2003, "Bacterial coaggregation: an integral process in the development of multi-species biofilms," Trends in Microbiology 11(2):94-100.
Rickard et al., 2006, "Autoinducer 2: a concentration-dependent signal for mutualistic bacterial biofilm growth," Molecular Microbiology 60(6):1446-1456.
Rickard et al., 2008, "Autoinducer-2 is produced in saliva-fed flow conditions relevant to natural oral biofilms," Journal of Applied Micriobiology 105(6):2096-2103.
S Zhang, JEI Wright, N Ozber, H Uludag. "The Interaction of Cationic Polymers and Their Bisphosphonate Derivatives with Hydroxyapatite," Macromolecular Bioscience, vol. 7, 2007, pp. 656-670. (Year: 2007).
Sanni et al., 2015, "Bacterial attachment to polymeric materials correlates with molecular flexibility and hydrophilicity," Adv. Healthcare Mater. 4(5):695-701.
Sauerbrey, 1959, "The use of quartz oscillators for weighing thin layers and for microweighing," Physics 155:206-222.
Shukla et al., 2010, "Controlling the release of peptide antimicrobial agents from surfaces," Biomaterials 31(8):2348-2357.
Sutherland, 2001, "The biofilm matrix—an immobilized but dynamic microbial environment," Trends in Microbiology 9(5):222-227.
Tahmassebi et al., 2006, "Soft drinks and dental health: a review of the current literature," J. Dentistry 34(1):2-11.
Uskokovic et al., 2010, "Nanosized hydroxyapatite and other calcium phosphates: Chemistry of formation and application as drug and gene delivery agents," J. Biomedical Materials Research Part B: Applied Biomaterials 96B(1):152-191.
Malle-Delgado et al., 2005, "Hydration forces between silica surfaces: experimental data and predictions from different theories," The J. Chemical Physics 123(3):34708.
Venault et al., 2014, "Bacterial resistance control on mineral surfaces of hydroxyapatite and human teeth via surface charge-driven antifouling coatings," ACS Appl. Mater. Interfaces 6(5):3201-3210.
Vogt et al., 2004, "Effect of Film Thickness on the Validity of the Sauerbrey Equation for Hydrated Polyelectrolyte Films," J. Physics Chemistry B 108(34):12685-12690.
Vroom et al., 1999, "Depth penetration and detection of pH gradients in biofilms by two-photon excitation microscopy," Appl. Environ. Microbiol. 65(8):3502-3511.
Wong et al., 2010, "Dual functional polyelectrolyte multilayer coatings for implants: permanent microbicidal base with controlled release of therapeutic agents," J. American Chemical Society 132(50):17840-17848.
X-Q Wang, Q Zhang. "pH-sensitive polymeric nanoparticles to improve oral bioavailability of peptide/protein drugs and poorly water-soluble drugs." European Journal of Pharmaceutics and Biopharmaceutics, vol. 82, 2012, pp. 219-229. (Year: 2012).
Z Cao, PI Gordiichuk, K Loos, EJR Sudholter, LCPM de Smet. "The effect of guanidinium functionalization on the structural properties and anion affinity of polyelectrolyte multilayers." Soft Matter, vol. 12, 2016, pp. 1496-1505, published online Nov. 24, 2015. (Year: 2015).
Zasloff, 2002, "Antimicrobial peptides of multicellular organisms," Nature 415(6870):389-395.
Zhu et al., 2015, "Layer-by-layer assemblies for antibacterial applications," Biomater Sci. 3(12):1505-1518.
Zhu et al., 2015, "Polyion multilayers with precise surface charge control for antifouling," ACS Appl. Mater. interfaces 7(1):852-861.
Zong et al., 2013, "Adsorption/Desorption Processes of pH-Responsive Copolymers on Model Dental Surfaces via QCM and AFM Analysis," ACS Symposium Series vol. 1148, Chapter 17, pp. 301-318.

* cited by examiner

ORAL CARE COMPOSITIONS AND METHODS FOR ANTI-ATTACHMENT POLYMERS AND COATINGS

This application is a continuation of United States application Ser. No. 15/788,852, filed Oct. 20, 2017, which issued as U.S. Pat. No. 10,653,149 on May 19, 2020, which claims priority benefit of U.S. Provisional Application No. 62/410,483, filed Oct. 20, 2016.

BACKGROUND

Biofilm formation on surfaces of an oral cavity, such as surfaces of teeth, is often contingent upon attachment of bacteria onto the salivary pellicle on the surfaces of the teeth. The biofilm formation resulting from the over accumulation of the bacteria on the surfaces of the teeth is implicated in a number of oral conditions and/or diseases (e.g., dental caries, gingivitis, periodontitis, halitosis, etc.). Accordingly, preventative or prophylactic approaches are often utilized to prevent the formation of the biofilm. For example, fluoride is often utilized in oral care compositions (e.g., toothpaste, mouthwashes, etc.) to prevent demineralization of the enamel of teeth.

While the prophylactic approaches have demonstrated efficacy in reducing the biofilm formation, these prophylactic approaches are only effective in the short-term. As such, recent efforts have focused on depositing coatings that resist bacterial adhesion on the surfaces of the teeth. For example, the deposition of positively charged polymeric coatings on the surfaces of the teeth has been demonstrated to reduce the viability of bacteria. The resulting net positive surface charge on the teeth, however, induced relatively increased bacterial adhesion due to the negatively charged bacterial cell wall.

What is needed, then, are improved compositions and methods for depositing or coating an antimicrobial or antibacterial composition on a substrate to prevent and/or inhibit microbial adhesion.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an antimicrobial or antibacterial composition including a cationic polymer having a poly-allylamine backbone, where at least a portion of the poly-allylamine backbone is functionalized. The poly-allylamine backbone may be functionalized with at least one of a guanidine functional group and a biguanide functional group.

In at least one embodiment, the poly-allylamine backbone is functionalized with the guanidine functional group.

In at least one embodiment, at least 50% of the poly-allylamine backbone is functionalized with the guanidine functional group.

In another embodiment, at least 67% of the poly-allylamine backbone is functionalized with the guanidine functional group.

In another embodiment, at least 75% of the poly-allylamine backbone is functionalized with the guanidine functional group.

In at least one embodiment, the poly-allylamine backbone is functionalized with the biguanide functional group.

In at least one embodiment, at least 50% of the poly-allylamine backbone is functionalized with the biguanide functional group.

The foregoing and/or other aspects and utilities embodied in the present disclosure may also be achieved by providing an oral care composition including an orally acceptable vehicle and any one or more of the antimicrobial or antibacterial compositions described in any one or more of the previous paragraphs.

In at least one embodiment, the antibacterial composition of the oral care composition does not include any anionic polymers.

In at least one embodiment, the oral care composition is a mouthwash or a toothpaste.

The foregoing and/or other aspects and utilities embodied in the present disclosure may also be achieved by providing a cleansing composition including a soap and any one or more of the antibacterial compositions described in any one or more of the previous paragraphs.

The foregoing and/or other aspects and utilities embodied in the present disclosure may also be achieved by providing an antimicrobial or antibacterial composition including a substrate and a cationic polymer deposited on a surface of the substrate. The cationic polymer may include a poly-allylamine backbone, and at least a portion of the poly-allylamine backbone may be functionalized with at least one of a guanidine functional group and a biguanide functional group.

The foregoing and/or other aspects and utilities embodied in the present disclosure may also be achieved by providing a method for deposition an antimicrobial or antibacterial composition on a substrate. The method may include contacting the substrate with a first polymer to physically adsorb the first polymer to surfaces of the substrate and form a first polymer layer. The first polymer may be a cationic polymer having a poly-allylamine backbone, and at least a portion of the poly-allylamine backbone may be functionalized with at least one of a guanidine functional group and a biguanide functional group.

In at least one embodiment, the method may include contacting a second polymer with the first polymer layer to physically adsorb the second polymer on the first polymer layer.

In at least one embodiment, contacting the second polymer with the first polymer layer decreases a thickness of the first polymer layer.

In at least one embodiment, the method further includes at least partially cross-linking the first polymer and the second polymer with one another.

In another embodiment, the second polymer is an anionic polymer, and the anionic polymer may include at least one of anhydride monomers, acrylate monomers, and phosphate-bearing monomers.

In at least one embodiment, the anionic polymer includes a copolymer, and the copolymer may be a polyvinylmethylether/maleic anhydride (PVM/MA) copolymer.

In at least one embodiment, the anionic polymer may include at least one of a linear polycarboxylate polymer.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

Figure 1A:
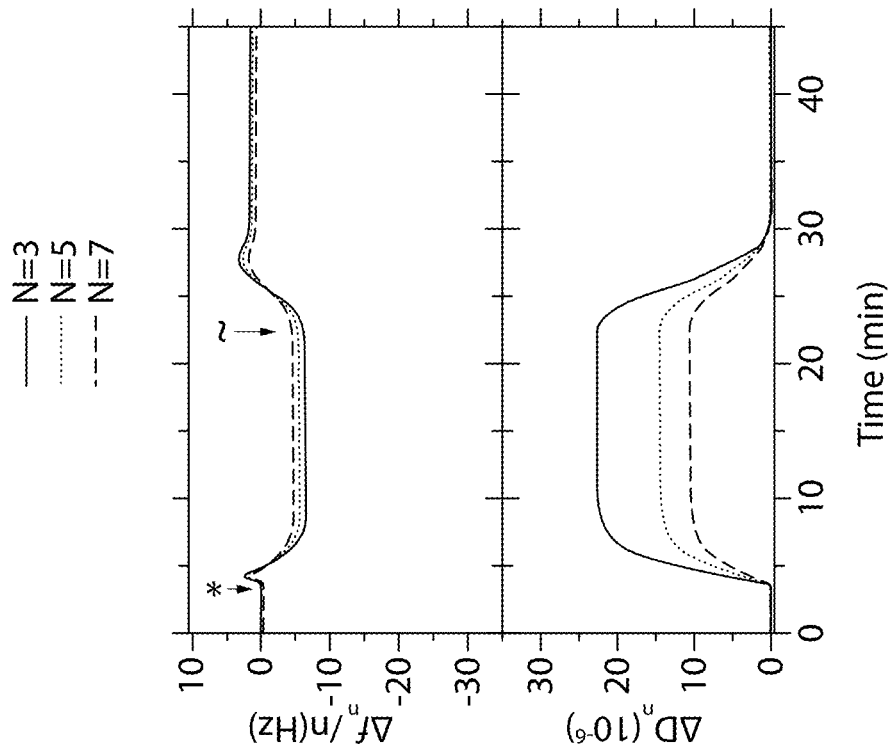
FIGS. 1 (a)-(d) illustrate plots of quartz-crystal microbalance with dissipation (QCM-D) studies for Example 1.

The following description of various preferred aspect(s) is merely exemplary in nature and is in no way intended to limit the invention, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

The present inventors have surprisingly and unexpectedly discovered cationic polymers including both amine and guanidine monomers (e.g., PAA-G75) readily physically adsorb on hydroxyapatite (HA) surfaces. The present inventors have also surprisingly and unexpectedly discovered that the morphology of the cationic polymers including both the amine and guanidine monomers is pH dependent. Particularly, the cationic polymers swell at low pH and collapse at high pH. It has also been surprisingly and unexpectedly discovered that an anionic polymer may be subsequently physically adsorbed onto the cationic polymer layer, and that the subsequent physical adsorption of the anionic polymer results in a decrease in thickness of the polymer layer. The decrease in the thickness of the polymer layer upon subsequent adsorption of the anionic polymer is at least partially dependent upon the electrostatic cross-linking between the anionic and cationic polymers. It has further been surprisingly and unexpectedly discovered that HA surfaces pretreated with artificial saliva (AS) exhibit relatively strong or increased adsorption of the cationic polymer including both amine and guanidine monomers as compared to the anionic polymers. It has further been surprisingly and unexpectedly discovered that the physical adsorption of the cationic polymer onto and/or into a pellicle layer (i.e., HA surface treated with human saliva) was relatively greater (e.g., ~2× more) as compared to the HA surfaces pretreated with AS.

In addition to the foregoing, the present inventors have surprisingly and unexpectedly discovered that cationic polymers immobilized, physically adsorbed, or otherwise deposited onto surfaces (e.g., oral cavity surfaces, homecare surfaces, skin, etc.) of varying substrates exhibit relatively decreased bacterial adherence as compared to anionic polymers (e.g., GANTREZ®). Particularly, it has been surprisingly and unexpectedly discovered that adsorbed cationic polymers including both amine and guanidine monomers (e.g., PAA-G75) exhibit relatively decreased bacterial adherence as compared to adsorbed anionic polymers (e.g., GANTREZ®). It has also been surprisingly and unexpectedly discovered that the adsorbed cationic polymers exhibit relatively decreased bacterial adherence as compared to hybrid anionic and cationic polymers adsorbed onto the surfaces (e.g., GANTREZ®/PAA-G75 treated surfaces). It has further been surprisingly and unexpectedly discovered that coatings formed from alternating the deposition of the anionic polymer and the cationic polymer onto the substrates exhibit relatively decreased bacterial adherence as compared to the anionic polymer alone. The relatively decreased bacterial adherence of the adsorbed cationic polymers suggests the utility of the cationic polymers as an anti-biofilm material or molecule for personal care and homecare applications. For example, the antibacterial adherence of the cationic polymer may have utility in oral care compositions (e.g., toothpastes, mouthrinses, etc.) to prevent the adherence of bacteria common to surfaces of the oral cavity, such as surfaces of teeth. In another example, the cationic polymer may have utility in homecare compositions (e.g., surface cleaners, disinfectants, etc.) to prevent the adherence of bacteria to the treated surfaces.

Compositions

Compositions disclosed herein may be antimicrobial or antibacterial compositions. The compositions may include one or more cationic polymers, one or more anionic polymers, and combinations thereof. For example, the composition may include a cationic polymer. In another example, the composition may include an anionic polymer. In yet another example, the composition may include a cationic polymer and an anionic polymer. The composition may include a single layer or a plurality of layers immobilized, physically adsorbed, or otherwise deposited on a substrate. Each of the layers may be or include the cationic polymer, the anionic polymer, and combinations thereof. For example, the composition may include a first layer of the cationic polymer immobilized on the substrate. In another example, the composition may include a first layer of the anionic polymer immobilized on the substrate. In another example, the composition may include a first layer of the cationic polymer immobilized on the substrate and a second layer of the anionic layer deposited on the cationic polymer. In yet another example, the composition may include a first layer of the anionic polymer immobilized on the substrate and a second layer of the cationic layer deposited on the anionic layer. The first layer and the second layer may at least partially cross-link with one another.

Cationic Polymers

The composition disclosed herein may include one or more cationic polymers. The one or more cationic polymers may include, cationic polymers having a poly-allylamine backbone. Illustrative cationic polymers, may include, but are not limited to, polyallylamine, polyallylguanidine, polylysine, and the like, and combinations thereof. At least a portion of the poly-allylamine backbone may be derivatized with one or more guanidine functional groups and/or one or more biguanide functional groups. For example, the cationic polymer may be represented by formula (1).

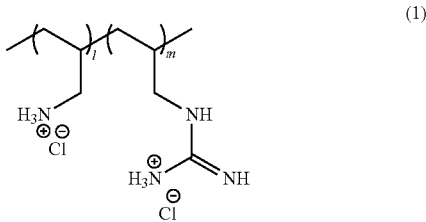

In at least one embodiment, the amount of the guanidine functional groups on the poly-allylamine backbone of the cationic polymer may be greater than or equal to about 0% and less than or equal to about 50%. For example, the amount of the guanidine functional groups on the poly-allylamine backbone of the cationic polymer may be about 0%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 10%, about 15%, about 20%, or about 25% to about 30%, about 35%, about 40%, about 45%, about 46%, about 4'7%, about 48%, about 49%, about 49.1%, about 49.2%, about 49.3%, about 49.4%, about 49.5%, about 49.6%, about 49.7%, about 49.8%, about 49.9%, or about 50%. In another example, the amount of the guanidine functional groups on the poly-allylamine backbone of the cationic polymer may be about 0% to about 50%, about 0.1% to about 49.9%, about 0.2% to about 49.8%, about 0.3% to about 49.7%, about 0.4% to about 49.6%, about 0.5% to about 49.5%, about 0.6% to about 49.4%, about 0.7% to about 49.3%, about 0.8% to about 49.2%, about 0.9% to about 49.1%, about 1% to about 49%, about 2% to about 48%, about 3% to about 4'7%, about 4% to about 46%, about 5% to about 45%, about 10% to about 40%, about 15% to about 35%, or about 20% to about 30%.

In another embodiment, the amount of the guanidine functional groups on the poly-allylamine backbone of the cationic polymer may be greater than or equal to about 50% and less than or equal to about 100%. For example, the amount of the guanidine functional groups on the poly-allylamine backbone of the cationic polymer may be about 50%, about 55%, about 60%, about 65%, or about 70% to about 75%, about 80%, about 85%, about 90%, about 95%, or about 100%. In another example, the amount of the guanidine functional groups on the poly-allylamine backbone of the cationic polymer may be from about 50% to about 100%, about 55% to about 95%, about 60% to about 90%, about 65% to about 85%, or about 70% to about 80%. In yet another example, the amount of the guanidine functional groups on the poly-allylamine backbone of the cationic polymer may be greater than 50%, greater than 55%, greater than 60%, greater than 65%, greater than 67%, greater than 70%, greater than 75%, greater than 80%, greater than 85%, greater than 90%, greater than 95%, greater than 98%, or greater than 99%. In a preferred embodiment, the amount of the guanidine functional groups on the poly-allylamine backbone of the cationic polymer may be about 75%. Accordingly, in at least one preferred embodiment, the cationic polymer may have a poly-allylamine backbone functionalized with about 75% guanidine, and about 25% amines.

The cationic polymer may have a weight average molecular weight at least partially determined by the amount of the guanidine functional groups contained on the poly-allylamine backbone. In at least one embodiment, the weight average molecular weight of the cationic polymer may be greater than or equal to about 5,000 Daltons (Da) and less than or equal to about 12,000 Da. For example, the cationic polymer may have a weight average molecular weight (MW, in Daltons) of about 5,000 Da to about 12,000 Da, about 5,500 Da to about 11,500 Da, about 6,000 Da to about 11,000 Da, about 6,500 Da to about 10,500 Da, about 7,000 Da to about 10,000 Da, about 7,500 Da to about 9,500 Da, or about 8,500 Da to about 9,000 Da. In another example, the cationic polymer may have a weight average molecular weight (MW, in Daltons) of about 5,000 Da, about 5,500 Da, about 6,000 Da, about 6,500 Da, about 7,000 Da, about 7,500 Da, or about 8,500 Da to about 9,000 Da, about 9,500 Da, about 10,000 Da, about 10,500 Da, about 11,000 Da, about 11,500 Da, or about 12,000 Da.

The cationic polymer may have a cationic character, or net positive charge, at an acidic pH, a neutral pH, and a basic or alkaline pH. For example, at an acidic pH of less than 7, at least a portion of the guanidine (pKa ~12) and amine functional groups may be protonated, thereby providing a net positive charge to the polymer. In another example, at a neutral pH of about 6 to about 7, at least a portion of the guanidine and amine functional groups may be protonated, thereby providing a net positive charge to the polymer. In yet another example, at an alkaline pH of greater than 7 to about 12, at least a portion of the guanidine and amine functional groups may be protonated. In an exemplary embodiment, the cationic polymer may maintain a net positive charge at a pH greater than or equal to about 1 and less than or equal to about 12.

The amount of the cationic polymer included in the composition may widely vary. In at least one embodiment, the amount of the cationic polymer included in the composition may be greater than or equal to about 1 wt % and less than or equal to about 100%. For example, the amount of the cationic polymer included in the composition may be about 1 wt %, about 2 wt %, about 3 wt %, about 4 wt %, about 5 wt %, about 10 wt %, about 15 wt %, about 20 wt %, about 25 wt %, about 30 wt %, about 35 wt %, about 40 wt %, about 45 wt %, about 50 wt %, or about 55 wt % to about 60 wt %, about 65 wt %, about 70 wt %, about 75 wt %, about 80 wt %, about 85 wt %, about 90 wt %, about 95 wt %, about 96 wt %, about 97 wt %, about 98 wt %, about 99 wt %, or about 100 wt %. In another example, the amount of the cationic polymer included in the composition may be about 1 wt % to about 100 wt %, about 2 wt % to about 99 wt %, about 3 wt % to about 98 wt %, about 4 wt % to about 97 wt %, about 5 wt % to about 96 wt %, about 10 wt % to about 95 wt %, about 15 wt % to about 90 wt %, about 20 wt % to about 85 wt %, about 25 wt % to about 80 wt %, about 30 wt % to about 75 wt %, about 35 wt % to about 70 wt %, about 40 wt % to about 65 wt %, about 45 wt % to about 60 wt %, or about 50 wt % to about 55 wt %. In yet another example, the amount of the cationic polymer included in the composition may be greater than 1 wt %, greater than 2 wt %, greater than 3 wt %, greater than 4 wt %, greater than 5 wt %, greater than 10 wt %, greater than 15 wt %, greater than 20 wt %, greater than 25 wt %, greater than 30 wt %, greater than 35 wt %, greater than 40 wt %, greater than 45 wt %, greater than 50 wt %, or greater than 55 wt % to greater than 60 wt %, greater than 65 wt %, greater than 70 wt %, greater than 75 wt %, greater than 80 wt %, greater than 85 wt %, greater than 90 wt %, greater than 95 wt %, greater than 96 wt %, greater than 97 wt %, greater than 98 wt %, greater than 99 wt %, or greater than 99.5 wt %.

Anionic Polymer

The composition disclosed herein may include one or more anionic polymers. In at least one embodiment, the anionic polymers may include polymers containing anhydride monomers, such as TAMOL 731 A, commercially available from Dow Chemical Co. of Midland, Mich. In at least one example, the one or more anionic polymers may include one or more copolymers, such as a polyvinylmethylether/maleic anhydride (PVM/MA) copolymer. In another example, the one or more anionic polymers may include an anionic linear polycarboxylate polymer, such as GANTREZ® S-97, commercially available from Ashland Specialty Chemicals of Bound Brook, N.J. In yet another example, the anionic polymers may include polymers having acrylic or methacrylic acid monomers, such as Rhodia DV8801. In an exemplary embodiment, the anionic polymers may include a polymer containing acrylate monomers and phosphate-bearing monomers. For example, the anionic polymer may be or include a copolymerized product of a mixture of acrylic acid, methacrylic acid, and 2-hydroxyethyl methacrylate phosphates. In at least one embodiment, the anionic polymers is the sodium salt of a copolymer of acrylic acid, methacrylic acid, or one or more of its simple esters, and methacryloylethyl phosphates.

The amount of the anionic polymer included in the composition may widely vary. In at least one embodiment, the amount of the anionic polymer included in the composition may be greater than or equal to about 0 wt % and less than or equal to about 50%. For example, the amount of the anionic polymer included in the composition may be about 0 wt %, about 1 wt %, about 2 wt %, about 3 wt %, about 4 wt %, about 5 wt %, about 6 wt %, about 7 wt %, about 8 wt %, about 9 wt %, about 10 wt %, about 15 wt %, or about 20 wt % to about 25 wt %, about 30 wt %, about 35 wt %, about 40 wt %, about 41 wt %, about 42 wt %, about 43 wt %, about 44 wt %, about 45 wt %, about 46 wt %, about 47 wt %, about 48 wt %, about 49 wt %, or about 50 wt %. In another example, the amount of the anionic polymer included in the composition may be about 0 wt % to about 50 wt %, about 1 wt % to about 49 wt %, about 2 wt % to about 48 wt %, about 3 wt % to about 47 wt %, about 4 wt % to about 46 wt %, about 5 wt % to about 45 wt %, about 6 wt % to about 44 wt %, about 7 wt % to about 43 wt %, about 8 wt % to about 42 wt %, about 9 wt % to about 41 wt %, about 10 wt % to about 40 wt %, about 15 wt % to about 35 wt %, or about 20 wt % to about 30 wt %. In yet another example, the amount of the anionic polymer included in the composition may be less than 0.1 wt %, less than 0.5 wt %, less than 1 wt %, less than 2 wt %, less than 3 wt %, less than 4 wt %, less than 5 wt %, less than 6 wt %, less than 7 wt %, less than 8 wt %, less than 9 wt %, less than 10 wt %, less than 15 wt %, less than 20 wt %, less than 25 wt %, less than 30 wt %, less than 35 wt %, less than 40 wt %, less than 41 wt %, less than 42 wt %, less than 43 wt %, less than 44 wt %, less than 45 wt %, less than 46 wt %, less than 47 wt %, less than 48 wt %, less than 49 wt %, or less than 50 wt %.

Substrate

In at least one embodiment, the substrate may be or include a medical material, device, dental implant, medical implant, or the like. In another embodiment, the substrate may be an oral cavity or a portion thereof. For example, the substrate may be enamel and/or teeth, gums, tongue, and/or cheek of the oral cavity. The substrate may be at least partially coated with saliva. The substrate and/or the saliva coated substrate may be coated with the cationic polymer and/or the anionic polymer.

Vehicle

The composition may form at least a portion of or be used in one or more oral care products, one or more homecare products, or compositions thereof. Illustrative oral care products may include, but are not limited to, a toothpaste (dentifrice), a prophylactic paste, a tooth powder, a tooth polish, a tooth gel, a chewing gum, a lozenge, a mouthwash, a whitening strip, a paint-on gel, varnish, veneer, and tube, syringe or dental tray including a gel or paste, or a gel or paste coated on an application support such as dental floss or a toothbrush (e.g., a manual, electric, sound, a combination thereof, or ultrasound toothbrush), and the like. Illustrative homecare products include, but are not limited to, all-purpose cleansers or cleaning solutions, heavy and light dish detergents, heavy duty detergents, light duty detergents, hard surface cleansers, spray cleansers, floor cleansers, bucket dilutable cleansers, microwave cleansers, stove-top cleansers, and the like.

In an exemplary embodiment, the composition may form at least a portion of or be used in a mouthwash. For example, the composition may include or be combined with an orally acceptable vehicle to form the oral care product (e.g., the mouthwash). In an exemplary embodiment, the orally acceptable vehicle may include a mixture of water, glycerin, sorbitol, and the like, and combinations thereof. In at least one embodiment, the orally acceptable vehicle may include water and glycerin. In at least one embodiment, the composition may be combined with a dual-phase orally acceptable vehicle including a hydrophilic phase and a hydrophobic phase, and optionally a hydrotrope to form a dual-phase mouthwash or a dual-phase mouthwash composition. The hydrophilic phase and the hydrophobic phase of the composition may be agitated or mixed to form a temporary oil-in-water emulsion that separates back into the hydrophobic and hydrophilic phases within five seconds to one hour after mixing. In another embodiment, the composition is combined with a single-phase orally acceptable vehicle including either a hydrophilic phase or a hydrophobic phase.

The hydrophobic phase of the orally acceptable vehicle may contain any orally acceptable hydrophobic liquid (e.g., generally recognized as safe). The orally acceptable hydrophobic liquids may include, but are not limited to, isopropyl myristate, mineral oil (e.g., white mineral oil, liquid paraffin, etc.), edible oils, or the like, or any combination thereof. Illustrative edible oils may include olive oil, corn oil, coconut oil, soybean oil, and combinations thereof. The hydrophobic phase may have an HLB of from 7 to 12, preferably an HLB of about 10. A preferred hydrophobic phase comprises heavy white mineral oil.

The hydrophilic phase of the orally acceptable vehicle may be an aqueous or water based phase. For example, the hydrophilic phase may have from about 40 wt % to about 95 wt % water. The hydrophilic phase may also include orally acceptable alcohols, humectants, and/or polymers. A humectant, on a pure humectant basis, may generally include about 10 wt % to about 50 wt %, or about 15 wt % to about 25 wt % of the oral care composition. In at least one embodiment, the cationic polymers may be included (solubilized and/or dispersed) in the hydrophilic phase.

As discussed above, the dual-phase mouthwash, including the hydrophilic phase and the hydrophobic phase, may optionally include a hydrotrope. The hydrotrope may include compounds that solubilize hydrophobic compounds in aqueous solutions. The hydrotrope may be a low molecular weight amphiphilic compound having a hydrophilic functional group and a low molecular weight hydrophobe. The hydrophobic functional group may attach to an organic moiety of the hydrophobic compounds to facility the solubility thereof in the aqueous solutions. Illustrative hydrotropes may include, but are not limited to, aromatic sulfonates, aromatic phosphate esters, glycerin, di- and polycarboxylates, polyglycols, and alcohols, including polyhydric alcohols.

Fluoride Ion Source

The composition may further include one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a preferred embodiment, the fluoride ion source includes sodium fluoride. The amount of the fluoride ion source in the oral care composition may be less than 0.08 wt %, less than 0.07 wt %, less than 0.06 wt %, less than 0.05 wt %, or less than 0.04 wt %. For example, the amount of the fluoride ion source may be about 0.05 wt %. In another embodiment, the fluoride ion source is present in an amount to provide a total of about 100 to about 20,000 ppm, about 200 to about 5,000 ppm, or about 500 to about 2,500 ppm, fluoride ions.

Surfactants

The composition may include one or more surfactants. For example, the composition may include one or more anionic surfactants, one or more cationic surfactants, one or more zwitterionic surfactants, one or more nonionic surfactants, and mixtures thereof. Examples of suitable surfactants may be found in U.S. Pat. No. 3,959,458 to Agricola et at, U.S. Pat. No. 3,937,807 to Haefele, and U.S. Pat. No. 4,051,234 to Gieske et al., the disclosures of which are incorporated herein by reference.

In at least one embodiment, the composition includes at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6-30}$ alkyl. For example, in a preferred embodiment the anionic surfactant is sodium lauryl sulfate. The anionic surfactants may also include higher alkyl-ether sulfates. For example, the anionic surfactants may have a formula $CH_3(CH_2)_mCH_2(OCH_2CH_2)_nSO_3X$, where m is 6-16, n is 1-6, and X is Na or K. In an exemplary embodiment, m is 10, and n is 2, 3, or 4, and X is Na or K. For example, the anionic surfactant may be sodium laureth-2 sulfate $(CH_3(CH_2)_{20}CH_2(OCH_2CH_2)_{20}SO_3Na)$. In another embodiment, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary embodiment, the anionic surfactant is a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In at least one embodiment, the composition may also include at least one nonionic surfactant. Accordingly, the composition may include at least one anionic surfactant, at least one nonionic surfactant, or both an anionic surfactant and a nonionic surfactant. The nonionic surfactant may function as an emulsifier. Illustrative nonionic surfactants may include, but are not limited to, poloxamers or the like. For example, the nonionic surfactants may include polysorbate 20, poloxamer 407, poloxamer 338, or the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred embodiment, the nonionic surfactant is PEG 40 hydrogenated castor oil, which is commercially available as CREMOPHOR® RH40 from BASF Corp. of Florham Park, N.J.

Chelating and Anti-Calculus Agents

The composition may optionally include one or more chelating agents and/or one or more anti-plaque agents. The chelating agents may be capable or configured to form complexes or bind with calcium found in cell walls of bacteria to weaken the cell walls and enhance or augment bacterial lysis. Illustrative anti-calculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, and diphosphonates. Illustrative chelating or anti-calculus agents may also include soluble pyrophosphates salts. In a preferred embodiment, the pyrophosphate salts of the oral care composition may be or include a alkali metal pyrophosphate salt. Illustrative alkali metal pyrophosphate salts include tetra alkali metal pyrophosphate, dialkali metal diacid pyrophosphate, trialkali metal monoacid pyrophosphate, and mixtures thereof, where the alkali metals are sodium or potassium. For example, in a preferred embodiment, the alkali metal pyrophosphate salts may be or include tetrasodium pyrophosphate and/or tetrapotassium pyrophosphate. The alkali metal pyrophosphate salts may be in either a hydrated form or a non-hydrated form.

Water

The oral care composition may include water. Water of the composition may be deionized and free of organic impurities. Water may make up the balance of the composition. For example, the amount of water in the composition may be from about 10 wt % to 90 wt %, about 40 wt % to about 85 wt %, or about 60 wt % to about 80 wt %. In another example, the amount of water in the composition may be at least 60 wt %, at least 65 wt %, at least 70 wt %, at least 78 wt %, or at least 79 wt %. The amount of water in the composition may include free water added and water introduced with other components or materials of the oral care composition. For example, the amount of the water in the composition may include free water and water associated with humectants, flavoring agents, or any other component of the composition.

pH Modifying Agents

The composition may optionally include one or more pH modifying agents. For example, the composition may include one or more acidifying agents or acids and/or one or more basifying agents or bases to reduce and/or increase the pH, respectively. The composition may also include one or more buffering agents or buffers to control or modulate the pH within a predetermined or desired range. In at least one embodiment, the acidifying, basifying, and/or buffering agents may be include in the composition to provide the composition with a pH between 2 to 10, 2 to 8, 3 to 9, 4 to 8, 6 to 10, or 7 to 9. Any orally acceptable pH modifying agent may be used, including without limitation carboxylic acid (e.g., citric acid), phosphoric acid, and sulfonic acid, acid salts (e.g., monosodium citrate, disodium citrate, monosodium malate, sodium dihydrogen phosphate, etc.), alkali metal hydroxides, such as sodium hydroxide, carbonates, such as sodium carbonate, bicarbonates, sesquicarbonates, borates, silicates, phosphates (e.g., monosodium phosphate, trisodium phosphate, pyrophosphate salts, etc.), imidazole, organic acids (e.g., lactic acid, etc.), and the like, and mixtures thereof. The one or more pH modifying agents may be optionally present in an amount effective to maintain the composition in an orally acceptable pH range.

Methods

In one or more embodiments, the present disclosure provides methods for physically adsorbing one or more layers of the cationic polymer and/or the anionic polymer onto the substrate. The present disclosure may also provide methods for depositing an antimicrobial or antibacterial composition or coating on the substrate. The present disclosure may also provide methods for fabricating or producing an antimicrobial or antibacterial coating on the substrate. The present disclosure may further provide methods for preventing or inhibiting microbial adhesion on the substrate. The method may include contacting the substrate with the cationic polymer or the anionic polymer to physically adsorb the cationic polymer or the anionic polymer on surfaces of the substrate and form a first layer. The method may also include contacting the cationic polymer or the anionic polymer with the first layer to at least partially cross-link the cationic polymer or the anionic polymer with the first layer.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

EXAMPLES

Example 1

The physisorption of an anionic polymer and a cationic polymer onto a surface was evaluated via quartz-crystal microbalance with dissipation (QCM-D). Particularly, the physisorption of GANTREZ® (i.e., the anionic polymer) and poly(allylamine-coallylguanidium (PAA-G75) (i.e., the cationic polymer) onto a hydroxyapatite (HA) surface was evaluated via QCM-D. To evaluate the physisorption of the anionic and cationic polymers, QCM-D sensor crystals that mimicked enamel (commercially available from Biolin Scientific, Inc., of Linthicum Heights, Md.) were utilized. The QCM-D sensor crystals were piezoelectric quartz crystal slides (14 mm diameter; 0.3 mm thickness) coated with 10 nm of nanocrystalline hydroxyl apatite $(Ca_{10}(PO_4)_6(OH)_2$ and 50 nm of silicon dioxide $(SiO_2)$. A $SiO_2$ coated QCM sensor crystal was used as a control.

Prior to adsorption of the anionic or the cationic polymers, the QCM-D sensor crystals were sterilized/cleaned to remove organic and biological impurities. Particularly, the QCM-D sensor crystals were exposed to UV-Ozone for 20 minutes (min) followed by immersion in 95% ethanol for 30 min at room temperature. Following the ethanol immersion, the QCM-D sensor crystals were rinsed with ultrapure water, dried with nitrogen, and further exposed to UV-Ozone for an additional 20 min.

To adsorb the anionic polymer (GANTREZ®) or the cationic polymer (PAA-G75) onto the QCM-D sensor crystals, 1.0 wt % polymer aqueous solutions (pH 7) of GANTREZ® and PAA-G75 were prepared and degassed via sonication. The QCM-D sensor crystals were then placed in respective flow cells, and the 1.0 wt % polymer aqueous solutions were circulated through the flow cells. QCM-D studies were then carried out with a QCM instrument (Model E4, Q-Sense Inc., Gothenburg, Sweden). The results of the QCM-D study are summarized in FIG. 1(a)-(d). In FIG. 1(a)-(d), the represents exposure of the surface to the respective polymer solution (either GANREZ® or PAA-G75), and the '~' represents exposure of the surface to deionized (DI) water.

FIG. 1(a) illustrates the results of the QCM-D study for GANTREZ® on a HA coated QCM sensor crystal. As illustrated in FIG. 1(a), upon exposure of the HA surfaces of the QCM sensor crystal to the 1.0 wt % GANTREZ®, the frequency ($\Delta f_3/3$) decreased from 0 to 15 and the dissipation ($\Delta D_3$) increased from 0 to 25. After rinsing with DI water, the frequency ($\Delta f_3/3$) increased from −15 to −5, but not back to its original value of 0. Additionally, after rinsing with DI water, the dissipation ($\Delta D_3$) decreased from 25 to 16. The results of FIG. 1(a) indicated that a viscoelastic layer of GANTREZ® was coating the HA surface of the QCM-D sensor crystals. The results further indicated that, after rinsing, weakly adsorbed GANTREZ® was released from the HA surface under the flow conditions used (flow rate=100 µL/min; Temp=21° C.; pH 7), and tightly adsorbed GANTREZ® remained on the HA surfaces and retained a viscoelastic character ($\Delta D_{3,5,7}$=16, 10, 7) at this flow condition.

Figure 1B:
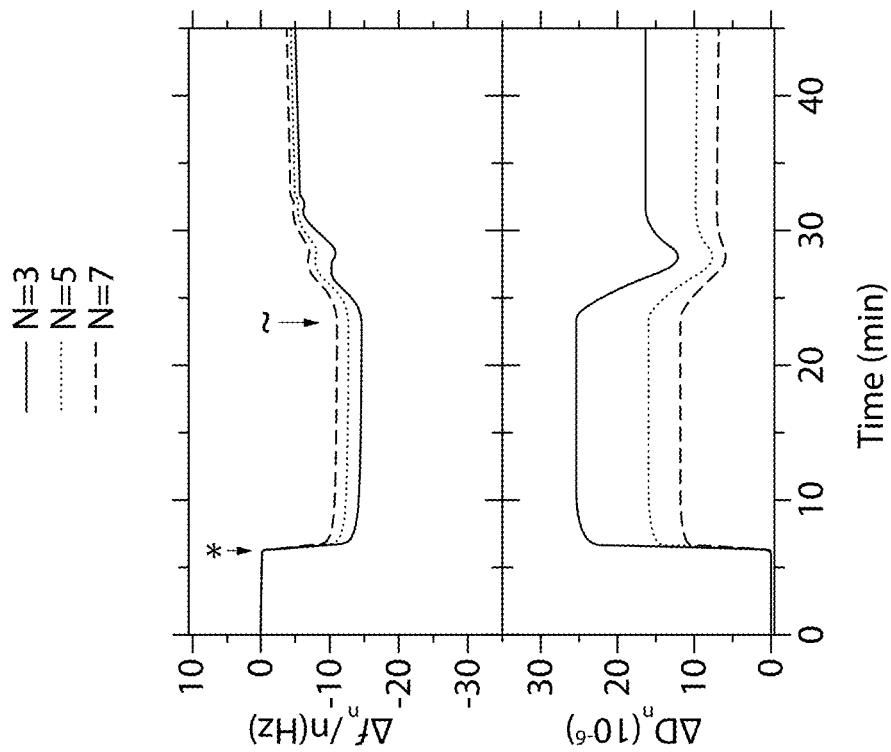

FIG. 1(b) illustrates the results of the QCM-D study for GANTREZ® on a $SiO_2$ coated QCM sensor crystal (Control). As illustrated in FIG. 1(b), the frequency ($\Delta f_3/3$) and dissipation ($\Delta D_3$) measured via the QCM-D exhibited similar behavior to FIG. 1(a). Upon exposure of the $SiO_2$ surface (Control) to the 1.0 wt % GANTREZ® solution, the frequency ($\Delta f_3/3$) decreased and the dissipation ($\Delta D_3$) increased. After the rinsing step, however, the frequency ($\Delta f_3/3$) and dissipation ($\Delta D_3$) returned to their original values (i.e., 0). FIG. 1(b) indicates that GANTREZ® adheres weakly to the $SiO_2$ surface and is easily removed during the rinsing step.

Figure 1C:
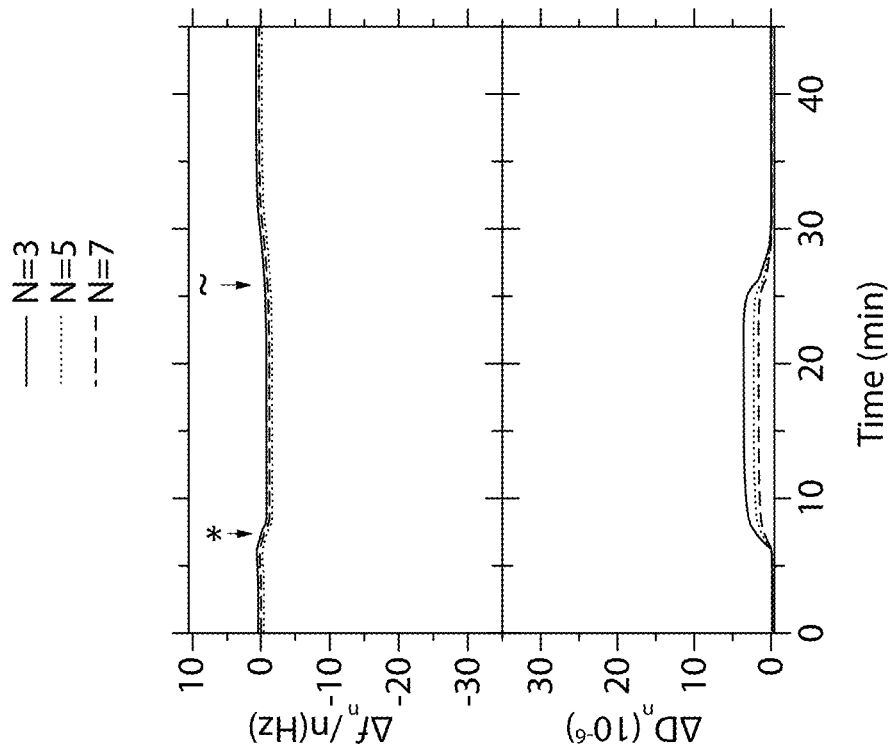

FIG. 1(c) illustrates the results of the QCM-D study for PAA-G75 on a HA coated QCM sensor crystal. As illustrated in FIG. 1(c), upon exposure of the HA surfaces to the cationic polymer (PAA-G75), the frequency ($\Delta f_3/3$)

decreased from 0 to −14 and the dissipation ($\Delta D_3$) increased from 0 to 10. After rinsing with DI water, the frequency increased from −14 to −8 and the dissipation decreased from 5 to 0. FIG. 1(c) illustrates that the PAA-G75 readily adsorbs on the HA surfaces. FIG. 1(c) further illustrates that during and after rinsing, weakly adsorbed polymers were released from the HA surfaces leaving behind a tightly adsorbed PAA-G75 layer on the HA surfaces having an elastic (rigid) film ($\Delta D_{3,5,7} = \sim 0$) character.

Figure 1D:
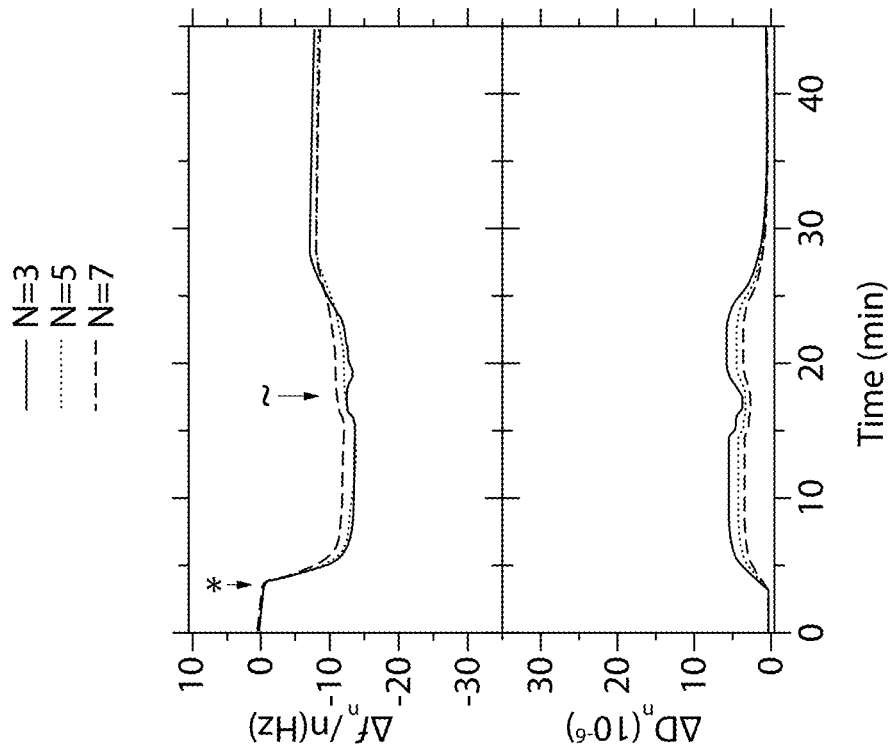

FIG. 1(d) illustrates the results of the QCM-D study for PAA-G75 on a $SiO_2$ coated QCM sensor crystal (Control). As illustrated in FIG. 1(d), upon exposure of the $SiO_2$ surfaces (Control) to the PAA-G75 solution, slight changes in the frequency and dissipation were observed. As further illustrated in FIG. 1(d), the frequency and dissipation returned to their original values (i.e., 0) after rinsing, indicating that PAA-G75 weakly interacts with the $SiO_2$ surfaces of the control.

Example 2

Saliva generally maintains the oral cavity at a pH between about 6.0 and about 7.5. The pH of the oral cavity, however, may vary due to the formation of biofilms and/or environmental factors (e.g., food and beverages). For example, the formation of biofilms on the surfaces of the teeth generates acidic microenvironments that may decrease the pH of the oral cavity. Additionally, the consumption of carbonated beverages may also decrease the pH of the oral cavity. Accordingly, the effects of the pH on the anionic polymer (GANTREZ®) and the cationic polymer (PAA-G75) adsorbed on the HA surfaces were evaluated. Particularly, the morphological changes, including the dry area mass ($ng/cm^2$) and the thickness (nm), of the anionic and cationic polymers were evaluated in situ for pH-dependent swelling via QCM-D under physiological pH and acidic pH environments. The results of the in situ evaluation of the pH-dependent swelling are summarized in Table 1.

TABLE 1 pH-dependent swelling of physically adsorbed ionic polymers on HA surfaces

| Polymer | Area mass[b] ($ng/cm^2$) | Grafting density (chains/$nm^2$) | $nm^2$/chain | Thickness (nm)[a] pH 3.5 | pH 7 |
|---|---|---|---|---|---|
| GANTREZ ® | 1200 ± 94 | $0.056 \times 10^{-3}$ | 18854 | 46 | 52 |
| PAA-G75 | 460 ± 21 | 0.437 | 2 | 54 | 6 |
| GANTREZ ® + PAA-G75 | 1393 ± 63 | N/A | N/A | N/A | 8 |

[a]Thickness values were estimated using modeling simulated and experimental curves for $\Delta f_n/n$ (n = 3, 5, 7) and $\Delta D_n$ vs. time, which showed a good fit between the viscoelastic model (Voigt) and the experimental data
[b]Area mass measured by QCM-D based on dry layers As illustrated in Table 1, the dry area mass of GANTREZ® was about 1200±94 $ng/cm^2$, and the dry area mass of PAA-G75 was about 460±21 $ng/cm^2$. The results of the dry area masses indicated that the anionic polymer, GANTREZ®, which had the highest molecular weight, had the greatest area mass on the HA surfaces. Without being bound by theory, it is believed that both molecular weight and electrostatic interaction may at least partially determine the adsorption of the anionic and cationic polymers on the HA surfaces. The results of the study also indicated that at low pH (3.5), the physically adsorbed PAA-G75 layer swelled and became more viscous, whereas at higher pH (pH 7), the PAA-G75 layer was elastic and rigid. The results of the study also indicated that at a pH of about 3.5, the GANTREZ® polymer layer became less viscous, and at a pH of about 7, the GANTREZ® layer swelled and became more viscous.

As is evident from Table 1, at a pH of about 7, the thickness of the PAA-G75 layer was about 6 nm. Applicants note that the thickness of the PAA-G75 layer of about 6 nm was similar to the observed thickness of the PAA-G75 layer at a pH of about 5.5. As further indicated in Table 1, as the pH was decreased to about 3.5, the thickness of the PAA-G75 increased to about 54 nm. As the pH increased from about 3.5 to about 7, the thickness of the PAA-G75 decreased back to its original value of about 6 nm. Without being bound by theory, it is believed that the pH response of the PAA-G75 polymer may be at least partially determined by the protonation and deprotonation of the amine functional groups. Particularly, as the pH decreases, the amine functional groups become protonated, resulting in electrostatic repulsion and swelling.

As further illustrated in Table 1, at a pH of about 3.5, the in situ thicknesses of the GANTREZ® layer was about 46 nm. Upon increasing the pH from about 3.5 to about 7, the in situ thicknesses of the GANTREZ® layer return to its corresponding original values of about 52 nm. Without being bound by theory, it is believed that the pH response of the GANTREZ® layer may be at least partially determined by the protonation and deprotonation of the carboxylic acid functional groups of the polymer. Particularly, as the pH increases, the carboxylic acid functional group becomes deprotonated, resulting in electrostatic repulsion and swelling.

Example 3

The effects of the order in which the anionic polymer (GANTREZ®) and the cationic polymer (PAA-G75) were deposited onto the HA of the QCM-D sensor crystals were evaluated. Particularly, the thickness of the polymeric film formed from varying the order in which the anionic polymer (GANTREZ®) and the cationic polymer (PAA-G75) were deposited was evaluated. To evaluate the effects of the order, each of the QCM-D sensor crystals were immersed in respective flow cells and a 1.0 wt % solution of the first polymer (GANTREZ® or PAA-G75) was circulated through the flow cells until the first polymer was adsorbed on the HA. Subsequently, a 1.0 wt % solution of the second polymer (GANTREZ® or PAA-G75) was circulated through the flow cells. The results of each sequence (A) and (B) are summarized in Table 2 and FIGS. 2(a) and (b).

TABLE 2

Effect of order of addition on film thickness of polymer

| Sequence | 1st Polymer | Thickness (nm) | 2nd Polymer | Thickness (nm) |
|---|---|---|---|---|
| A | GANTREZ ® | 54 | PAA-G75 | 8 |
| B | PAA-G75 | 9 | GANTREZ ® | 57 → 19 [a] |

[a] The film thickness decreased from 57 nm to 19 nm over a period of one hour.

In sequence (A), exposure of the HA to GANTREZ® resulted in a viscoelastic polymer layer having a thickness of about 54 nm, and the subsequent exposure to the PAA-G75 solution resulted in an immediate collapse of the thickness from 54 nm to about 8 nm. Without being bound by theory, it is believed that the decrease in the thickness observed in Sequence (A) resulted from strong electrostatic crosslinking between the oppositely charged polymers.

Figure 2A:
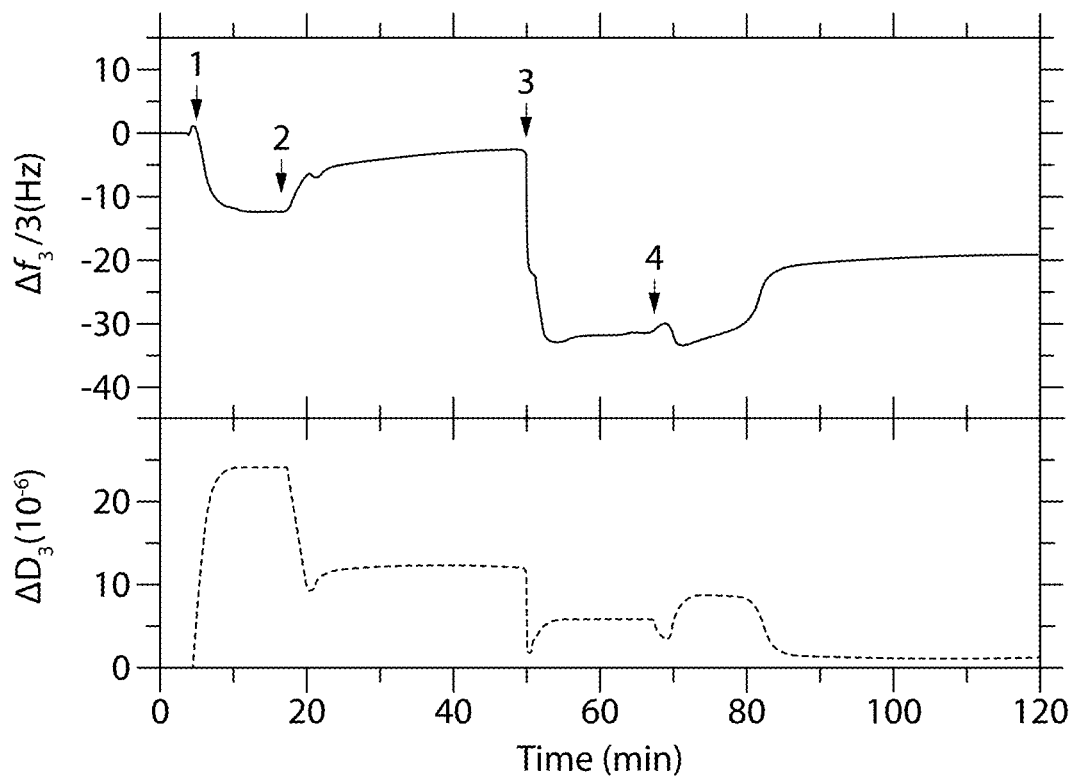
FIGS. 2 (a) and (b) illustrate plots of the QCM-D studies for Example 1.
Figure 2B:
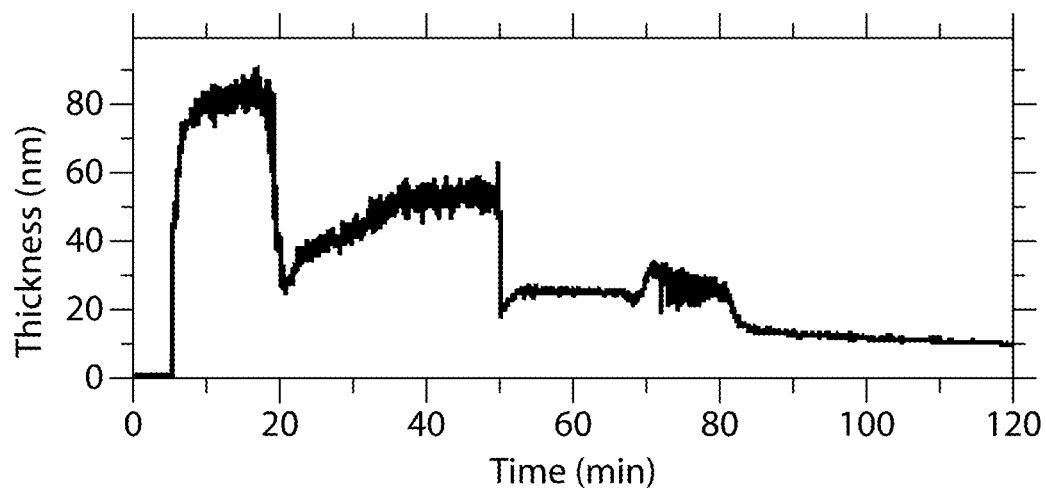

As illustrated in FIG. 2(a), upon the addition of the PAA-G75 (Arrow 3), the frequency and dissipation of the GANTREZ® layer decreased, indicating an increase in both mass and rigidity. Without being bound by theory, it is believed that the increase in mass is a direct result from the uptake of PAA-G75. Additionally, the increase in stiffness of the GANTREZ® layer is consistent with that of the PAA-G75 polymer, which indicates/confirms electrostatic crosslinking between the negatively charged carboxylate groups of GANTREZ® and the positively charged guanidinium (or amine) groups of PAA-G75. As further illustrated in FIG. 2(a), upon rinsing with DI water (pH 7) (Arrow 4), the frequency increased to about −20, and the dissipation decreased to about 4. The results indicated that the weakly adsorbed PAA-G75 polymer rinsed off from the composition/hybrid PAA-G75/GANTREZ® layers, and the film retained the rigid and elastic character due to strong electrostatic interactions between the anionic polymer (GANTREZ®) and the cationic polymer (PAA-G75).

In addition to the foregoing, according to the dry area mass of the PAA-G75 uptake by the GANTREZ® layer, determined using dry QCM-D technique and summarized in Table 1 above, the area mass of the GANTREZ® layer before and after cross-linking with PAA-G75 are 1200 ng/cm$^2$ and 1393 ng/cm$^2$, respectively. The results indicate that the mass amount of PAA-G75 that was adsorbed on/into the GANTREZ® layer by electrostatic ionic cross-linking was about 193 ng/cm$^2$. Accordingly, it is surprisingly and unexpectedly discovered that GANTREZ® adsorbs a relatively high amount of cationic polymers (e.g., PAA-G75) by forming ionic cross-linking with the cationic polymers. In this case, an 85% contraction of the GANTREZ® layer was observed upon exposure of the GANTREZ® layer to the PAA-G75.

In sequence (B), exposure of the HA to the PAA-G75 first resulted in the formation of a polymeric layer of about 9 nm, and subsequent exposure to the GANTREZ® resulted in the formation of a semi-viscoelastic composite layer of about 57 nm. As further indicated in Table 2, the composite layer collapsed from about 57 nm to about 19 nm over a period of 1 hour. The results indicated that when PAA-G75 is utilized as the first polymer, as in sequence (B), there is a significant period of rearrangement before a stable film is formed.

Accordingly, it was surprisingly and unexpectedly discovered that the order or sequence in which the cationic polymer (PAA-G75) and the anionic polymer (GANTREZ®) were exposed to the HA surface at least partially determined the film structure and the anti-attachment capabilities.

Example 4

The adsorption of the anionic polymer (GANTREZ®) or the cationic polymer (PAA-G75) on artificial saliva (AS) treated HA surfaces was evaluated via in situ and dry QCM-D. The results of the adsorption of the anionic and cationic polymers on the HA surfaces pretreated with AS are illustrated in FIGS. 3(a) and (b).

Figure 3A:
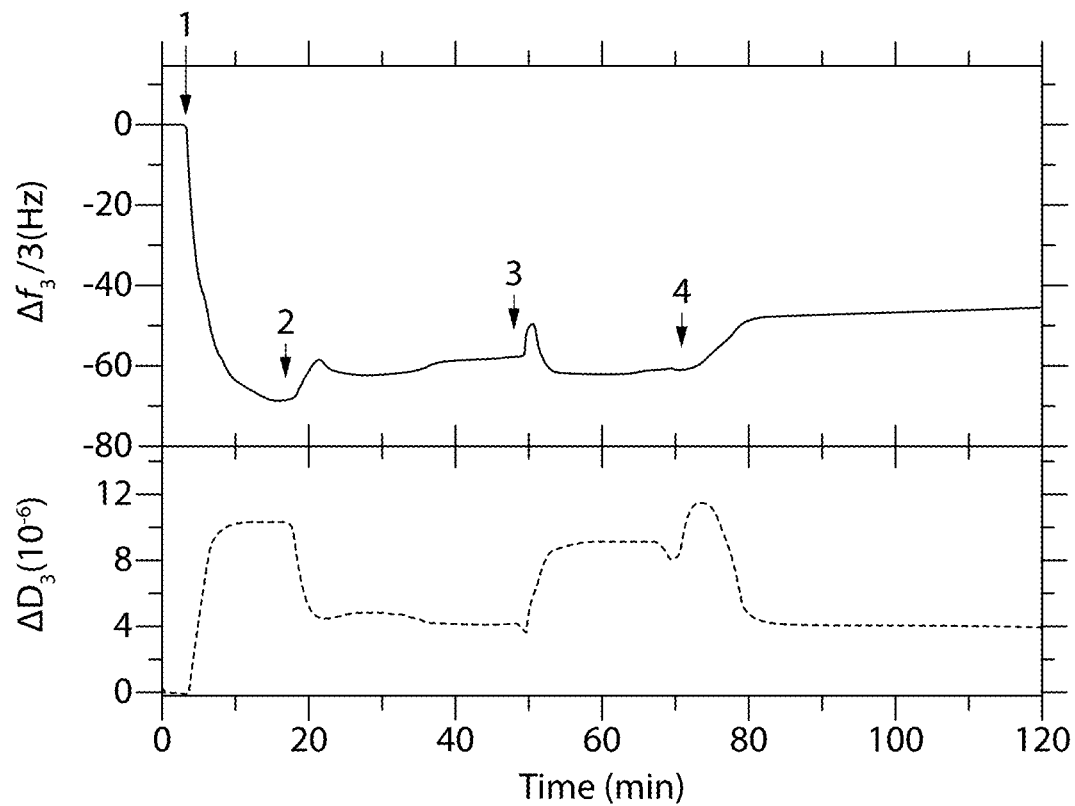
FIGS. 3 (a) and (b) illustrate plots of the QCM-D studies for Example 4.
Figure 3B:
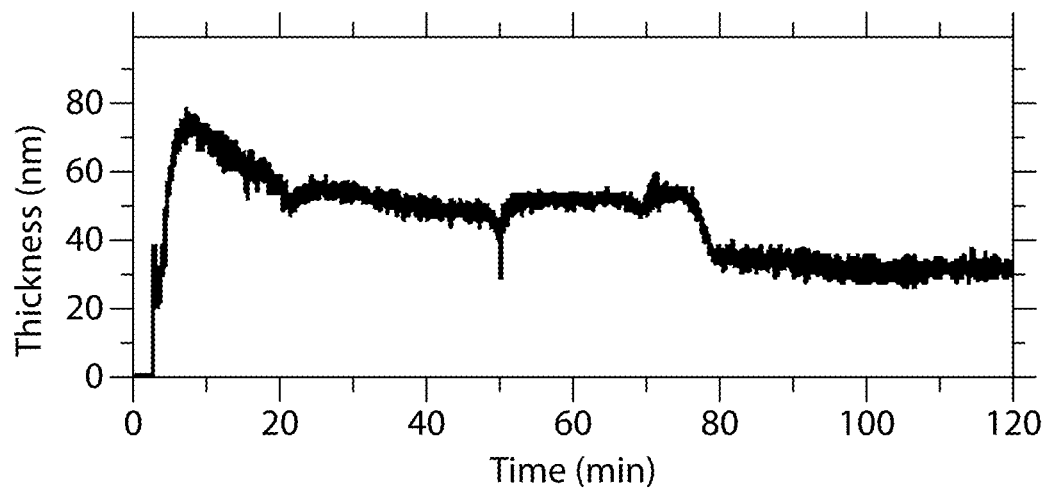

As illustrated in FIG. 3(a), upon exposing HA surfaces to the artificial saliva at 21° C. (Arrow 1), the frequency decreases to about −70 and the dissipation increases to about 10E-6. These results indicated that the adsorbed AS layer behaved viscoelastically. After rinsing the AS layer with DI water (Arrow 2), the frequency increased to about −60 and the dissipation decreased to about 4E-6, indicating the removal of loosely bound species and a stably attached AS layer. After exposure of the AS layer to the PAA-G75 (pH 7) (Arrow 3), followed by rinsing with DI water (Arrow 4), the dissipation was similar to that of the initially stable AS layer but the frequency increased to about −45. As illustrated in FIG. 3(b), the in situ thickness of the AS layer was about 25 nm, and the treatment of the PAA-G75 on the AS layer resulted in a decrease in layer thickness to about 16 nm. In contrast, exposure of the AS layer to the GANTREZ® solution and DI water had similar results (not shown). The area mass of the AS layer before and after exposure to the PAA-G75 was determined to be about 1249 ng/cm$^2$ and 1091 ng/cm$^2$, respectively, a decrease of about 158 ng/cm$^2$. The decrease in the area mass, however, may not suggest that the PAA-G75 polymer was not adsorbed by the AS layer, as the mass change could result from changes in the relatively small components, such as proteins, in the AS layer. Accordingly, colloid-probe Atomic Force Microscopy (AFM) techniques were utilized to measure the adsorption of the PAA-G75 polymer by the AS layer.

Example 5

As discussed above, the adsorption of the PAA-G75 polymer by the negatively charged AS layer was analyzed via colloid-probe AFM (Model MFP3D, Asylum Research, Santa Barbara, USA) by monitoring surface interactions of the PAA-G75 treated AS layer on the HA surfaces. Silica micro-beads (Microspheres-Nanospheres, Corpuscular, N.Y., USA) were attached to a tip-less cantilever (CSC12, Mikromash, USA) using a micromanipulator. A two-part epoxy (JB Weld, Sulphur Springs, Tex.) was used to affix the colloid to the end of the cantilever. The cantilevers were cleaned in ethanol and treated in UV-Ozone (UVO Cleaner model 42, Jelight Co. Inc., Irvine, Calif.) for at least 15 minutes before use. Colloids with the lowest available RMS roughness (~1.5-2 nm) were used for measurements.

Figure 4A:
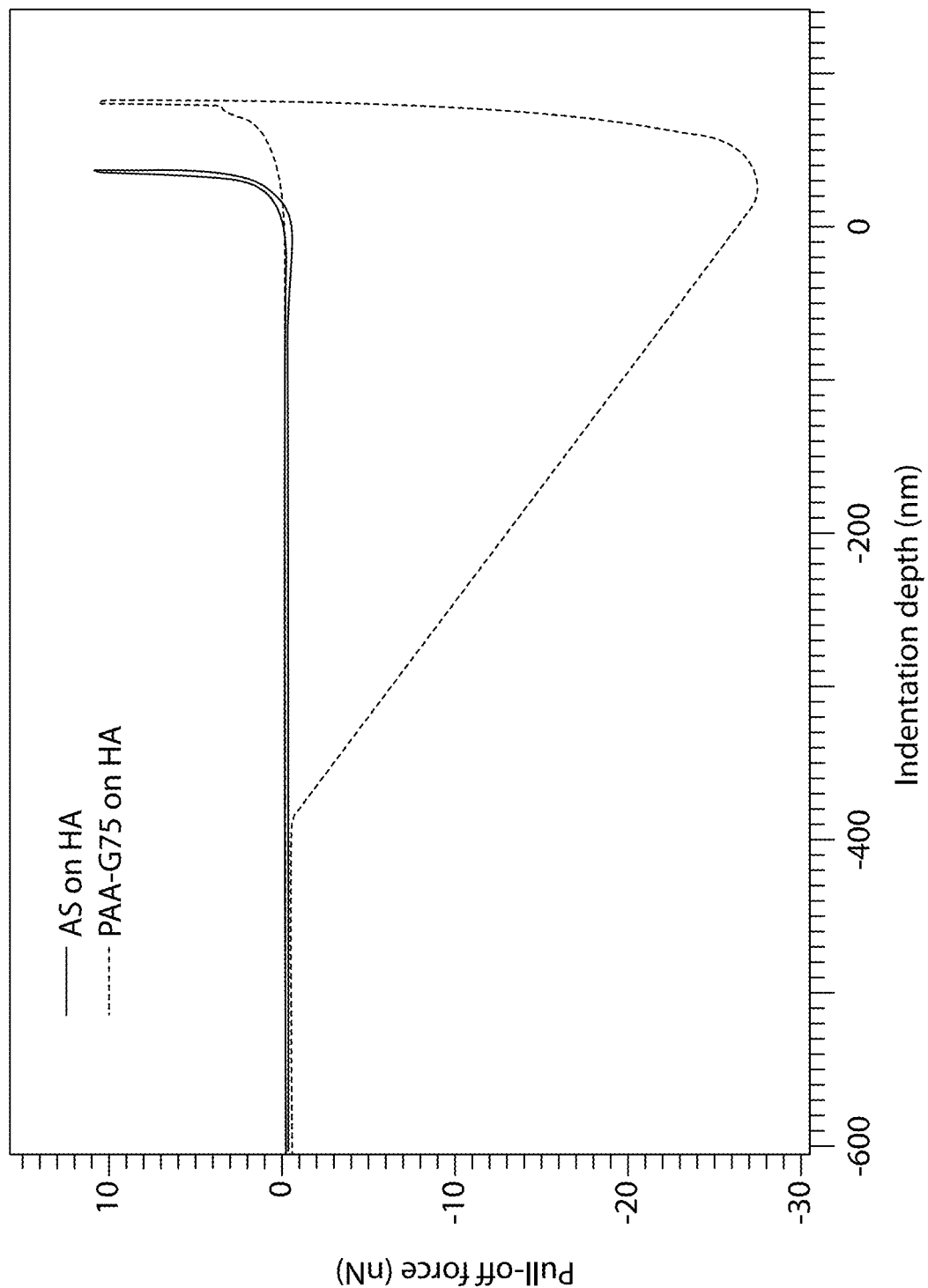
FIGS. 4 (a)-(c) illustrate Force and Distance (FD) curves of various single and composite films.
Figure 4B:
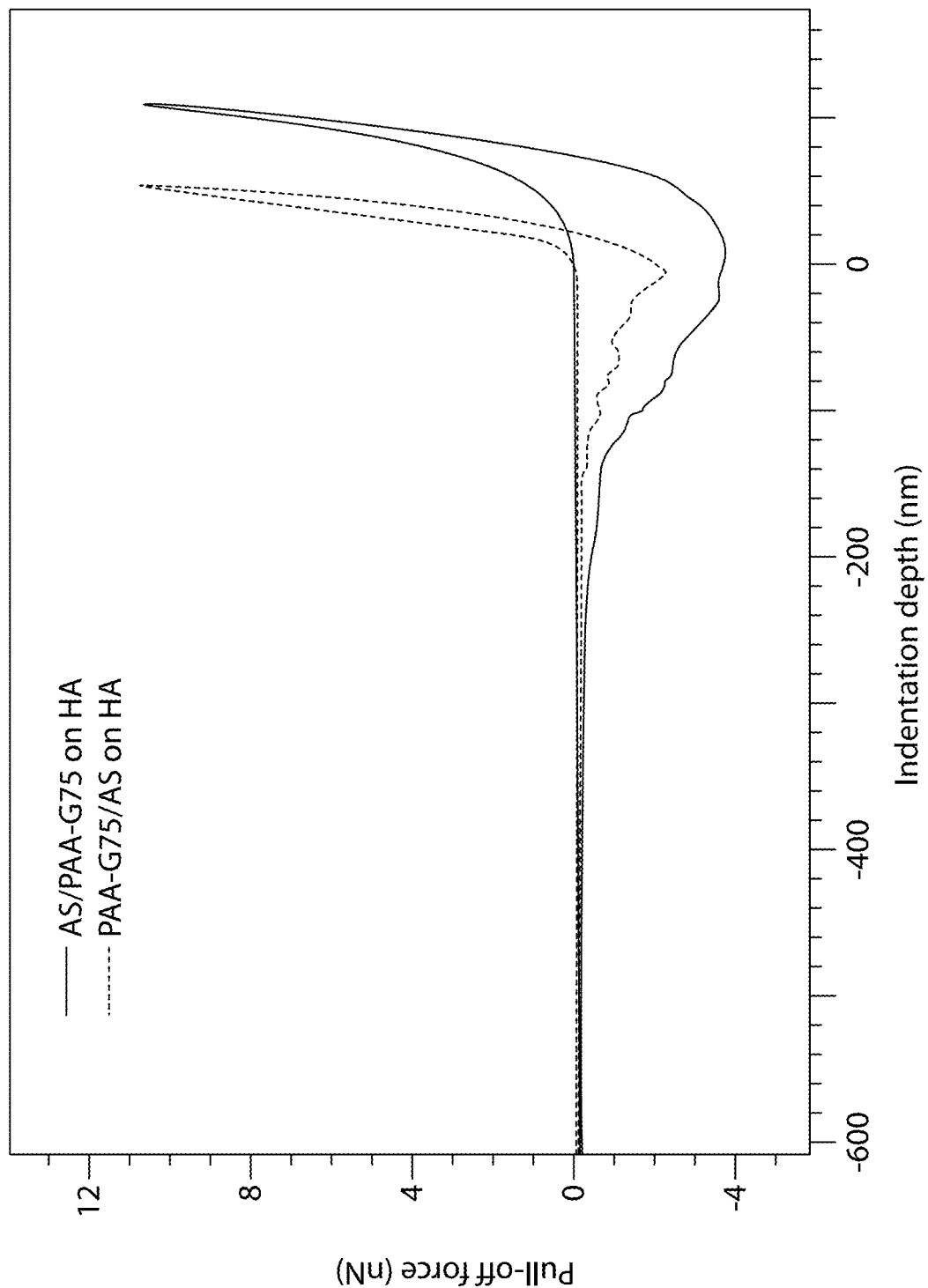
Figure 4C:
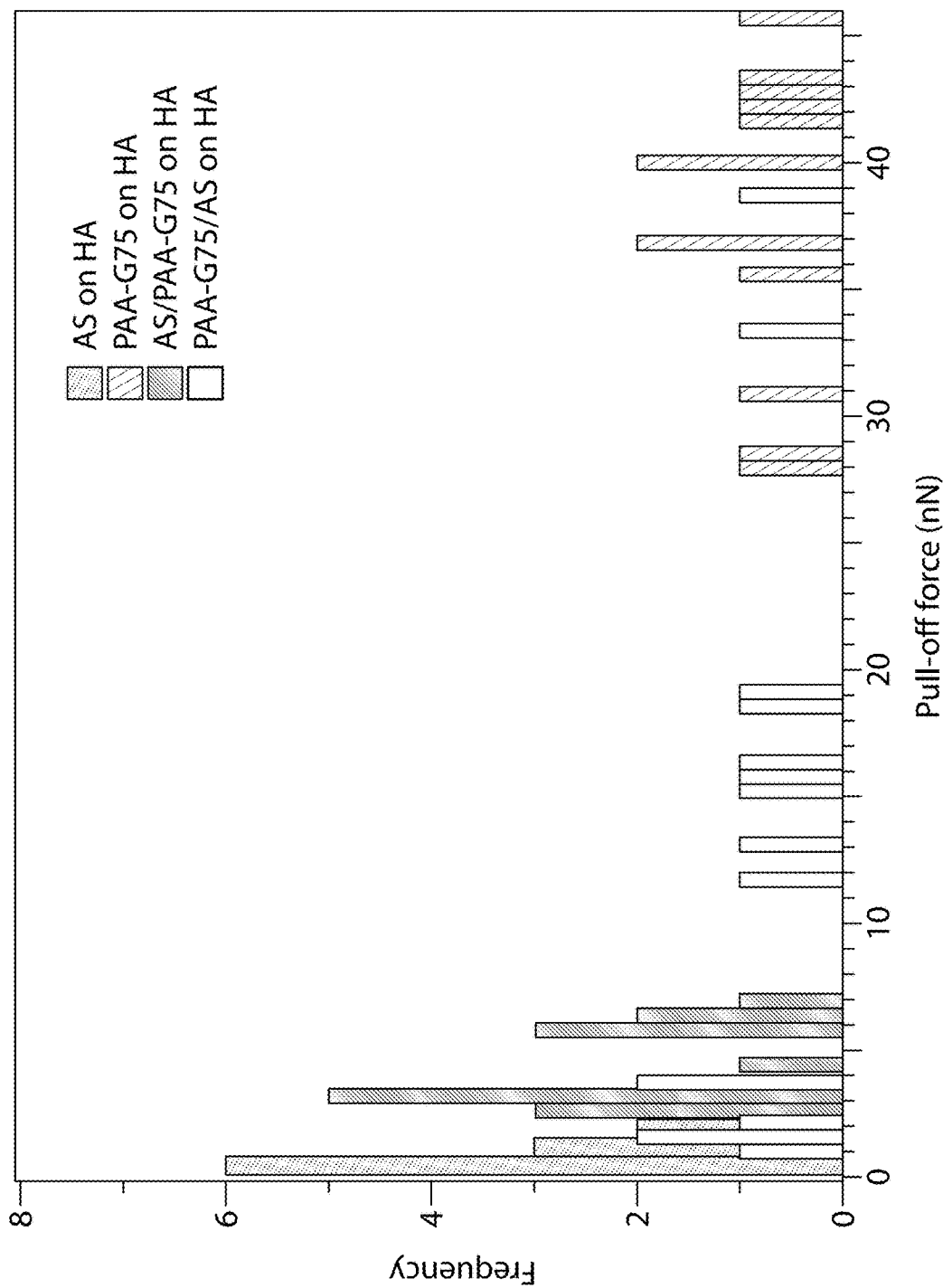

FIG. 4(a)-(c) illustrates the Force and Distance (FD) curves of various single and composite films. Particularly, FIG. 4(a) illustrates the FD curves for AS on HA and PAA-G75 on HA, and FIG. 4(b) illustrates the FD curves for AS(top)/PAA-G75 on HA, and PAA-G75(top)/AS on HA. FIG. 4(c) illustrates the spread of the pull-off forces measured upon retracting of the negatively-charged silica colloid probe from the film, and presents a qualitative comparison of the surface charges presented by the varying single and composite films.

As illustrated in FIG. 4(a), the cationic polymer (PAA-G75) exhibited high adhesion (~34.6±9.7 nN), while the bio-polymer chains of the negatively charged AS layer (mainly mucin) resulted in negligible adhesion (~1.0±0.3 nN) when probed with negatively-charged silica colloid at pH=7. As illustrated in FIG. 4(b), the composite or combined films of AS/PAA-G75 and PAA-G75/AS on HA films exhibited similar pull-off forces of about 4.5±1.7 nN and about 6.7+17.5 nN, respectively. AS/PAA-G75 films showed slightly greater adhesion than single AS films with minimum spread in the measured forces, indicating a negative-charge dominated surface. On the other hand, the magnitude and the spread of the pull-off forces observed for PAA-G75/AS layer on HA, as illustrated in FIG. 4(c), indicates the presence of both anionic and cationic groups on the surface.

The results indicate that exposure of the AS layer to the PAA-G75 solution and DI water for rinsing, adsorption of the PAA-G75 does occur. Accordingly, the PAA-G75 polymers are non-homogenously adsorbed and distributed onto and/or into the AS layer.

Example 6

The morphological changes of the HA surfaces after treatment with varying polymers were studied to evaluate the surface morphology and roughness via tapping mode AFM (Digital Instruments, Santa Barbara, Calif.: Dimension 3000 AFM). The tapping mode was evaluated with a single crystal Si tip with a spring constant of 48 N/m, a radius of curvature of about 10 nm, and a response frequency of approximately 190 kHz were used. AFM images were obtained over scan sizes of 1×1 µm$^2$ and 5×5 µm$^2$. The images were analyzed using Picoview 1.6 software (Agilent Technologies). The root mean square roughness ($R_{rms}$) values were determined from five separate 1 µm$^2$ images for each substrate type. The surface topography of the varying polymers physically adsorbed on the HA surface of the QCM-D sensor crystals are summarized in Table 3.

TABLE 3

Roughness Values

| # | Polymer Layers on QCM-D Crystals | RMS (nm) | STDEV |
|---|---|---|---|
| (1) | AS/HA | 1.7 | 0.3 |
| (2) | PAA-G75/HA | 2.1 | 0.3 |
| (3) | GANTREZ ®/HA | 1.0 | 0.1 |
| (4) | PAA-G75/AS/HA | 5.4 | 1.1 |
| (5) | GANTREZ ®/AS/HA | 2.9 | 0.4 |

As indicated in Table 3, the root mean square ($R_{rms}$) of the AS/HA (1), PAA-G75/HA (2), and GANTREZ®/HA (3) surfaces were about 1.7±0.3 nm, about 2.1±0.3 nm, and about 1.0±0.1 nm, respectively. The results indicated that the nano-crystalline particle shapes of HA are still observed under the polymer layers of each of these samples (1)-(3), and the roughness of the adsorbed polymer surfaces did not change significantly.

The surface morphology and roughness of the sequentially adsorbed polymer layers onto and/or into the first polymer adsorbed layer on the HA surface of the QCM-D sensor crystals (4) and (5) were also evaluated. With respect to the AS/HA (1) surface, the root mean square ($R_{rms}$) of the PAA-G75/AS/HA (4) increased from about 1.7±0.3 nm so 5.4±1.1 nm, and she root mean square ($R_{rms}$) of the GANTREZ®/AS/HA (5) increased from about 1.7±0.3 nm to about 2.9±0.4 nm.

The increase in the root mean square ($R_{rms}$) indicated that the sequential polymer treatments of either PAA-G75 or GANTREZ® on the AS layer changed the morphology and increased the roughness of the layers. Particularly, the highest roughness value of the PAA-G75/AS/HA (4) surface is consistent with the magnitude and spread of the pull-off forces observed in Example 5, indicating that the cationic polymer, PAA-G75, which has a relatively lower molecular weight, is non-homogenously adsorbed and distributed onto and/or into the AS layer, which is negatively charged. Additionally, the roughness of the GANTREZ®/AS/HA (5) surface is relatively lower than that of the PAA-G75/AS/HA (4) surface, which suggests that the anionic polymer (GANTREZ®), which has a higher molecular weight, is more homogenously adsorbed and distributed onto and/or into the negatively charged AS layer.

Example 7

The adsorption of PAA-G75 on the HA surface of a QCM-D sensor crystal pretreated with human saliva versus artificial saliva (AS) was evaluated under biomimetic conditions (37° C.) via in situ and dry QCM-D methods, the results of which are summarized in Table 4. As indicated in Table 4, the in situ thickness of the AS layer at 21° C. and at 37° C. were 25 nm and 28 nm, respectively. The results indicated that in situ QCM-D of the AS layer on HA at 37° C. was similar to those of the AS layer on HA at 21° C.

TABLE 4

Adsorption of PAA-G75 on pellicle versus AS layer using in situ and dry QCM-D.

| | Before PAA-G75 treatment (I) | | | After PAA-G75 treatment (II) | | | Area mass of |
|---|---|---|---|---|---|---|---|
| | In-situ QCM | | Dry QCM | In-situ QCM | | Dry QCM | Absorbed |
| Temp (37° C.) | Thickness (nm) | Viscosity ($10^{-3}$ Ns/m$^2$) | Area mass (ng/cm$^2$) | Thickness (nm) | Viscosity ($10^{-3}$ Ns/m$^2$) | Area mass (ng/cm$^2$) | PAA-G75 (ng/cm$^2$) |
| Pellicle | 15.7 ± 0.1 | 3.38 ± 0.02 | 869 ± 26 | 17.2 ± 0.2 | 2.03 ± 0.01 | 2581 ± 40 | 1712 ± 56 |
| AS | 28.1 ± 0.5 | 1.36 ± 0.01 | 792 ± 10 | 32.7 ± 1.0 | 1.33 ± 0.01 | 1658 ± 75 | 866 ± 85 |

At 21° C., thickness and area deposited mass of AS layer forming on HA surface are 25 nm and 1249 ng/cm$^2$, respectively; After PAA-G75 treatment, the thickness and areal mass of the treated layer are 16 nm and 1091 ng/cm$^2$, respectively.

As evident from Table 4, treatment of the PAA-G75 on the AS layer at 37° C. increased the layer thickness (33 nm) and decreased the layer viscosity (1.33E-3 Ns/m$^2$). In the dry QCM study, after treatment of the PAA-G75 on the AS layer at 37° C., the area mass of the adsorbed PAA-G75 onto and/or into the AS layer was 866 ng/cm$^2$. The results indicate that at 37° C., adsorption of the PAA-G75 by the AS layer is observed.

As further illustrated in Table 4, the in situ QCM-D traces of formation of the pellicle layer on HA at 37° C. were similar to those of formation of the AS layer on HA at 37° C. As shown in Table 4, the in situ thickness and viscosity of the pellicle layer were about 16 nm and about 3.4×10$^{-3}$ Ns/m$^2$. The pellicle layer had lower thickness and higher viscosity than the AS layer at 37° C. Treatment of the pellicle layer with the PAA-G75 polymer solution resulted in a small increase in the layer thickness (i.e., about 17 nm). In addition, the dry QCM study showed that after the treatment of the pellicle layer with the PAA-G75 polymer solution at 37° C., the area mass of adsorbed PAA-G75 on and/or into the pellicle layer was about 1712 ng/cm$^2$. These results indicated that adsorption of the PAA-G75 polymer by the pellicle layer was observed and the adsorbed amount of PAA-G75 onto and/or into the pellicle layer was about 2x more than that onto and/or into the AS layer. These studies show that polymer adsorption onto HA and saliva coated HA depends strongly on the polymer type and size and that there is an electrostatic interaction between polymer and saliva and/or oppositely charged polymers that stabilizes the coatings.

Example 8

The antimicrobial properties of the anionic polymer (GANTREZ®) and the cationic polymer (PAA-G75) were evaluated by adsorbing the anionic polymer and the cationic polymer on respective hydroxyapatite (HA) discs. To adsorb the anionic polymer and the cationic polymer on the HA discs, respective hydrated HA discs were incubated in a 1.0 wt % solution of fluorescein conjugated GANTREZ® or fluorescein conjugated PAA-G75 at a pH of about 7.2 for about 60 min. After incubation for about 60 min, the hydrated HA discs were washed in deionized water for about 5 min, and the adsorption of the anionic polymer and the cationic polymer was verified via confocal microscopy.

Figure 5A:
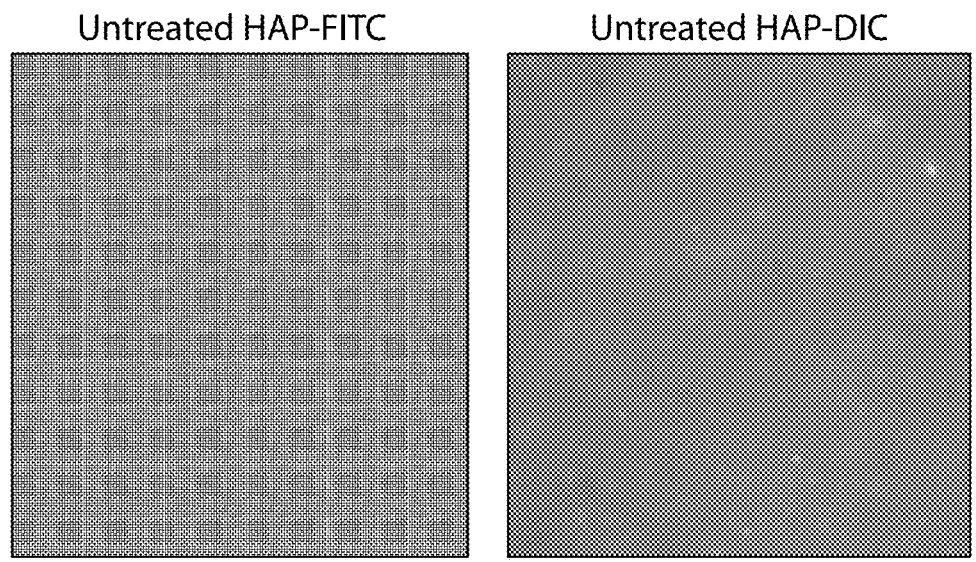
FIGS. 5 (a) and (b) illustrate confocal microscopy images for Example 8.
Figure 5B:
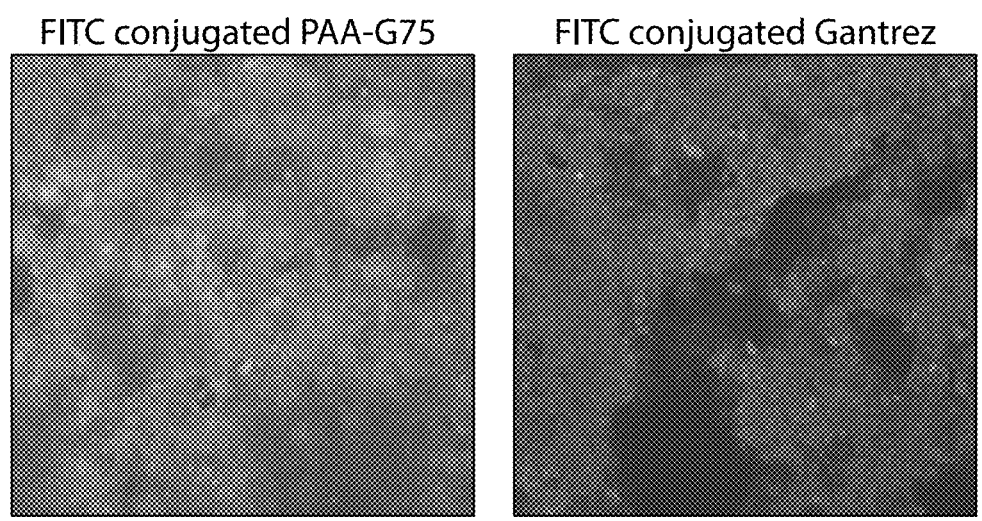

The results of the confocal microscopy are illustrated in FIGS. 5(a) and (b). Particularly, FIG. 5(a) illustrates the untreated HA discs, and FIG. 5(b) illustrates images obtained via confocal microscopy after adsorption of the fluorescein conjugated anionic and cationic polymers. As illustrated in FIG. 5(a), no autofluorescence was observed from the untreated HA discs. Further, as illustrated in FIG. 5(b), fluorescence analysis via confocal microscopy confirmed successful adsorption and retention of both the anionic polymer (GANTREZ®) and the cationic polymer (PAA-G75) on the surface of the HA discs.

Example 9

The antibacterial attachment performance of PAA-G75 against common bacterial biomass of the oral cavity was evaluated on the HA surface after adsorption of the anionic polymer (GANTREZ®) and/or the cationic polymer (PAA-G75). To evaluate the antibacterial attachment performance, hydrated HA discs were incubated at room temperature for 1 hour in a 1.0 wt % solution of either the anionic polymer (GANTREZ®) or the cationic polymer (PAA-G75) at a pH of about 7.2 to provide the GANTREZ® treated and the PAA-G75 treated HA discs, respectively. Additionally, separate Hydrated HA discs were also treated with both the GANTREZ® and the PAA-G75 to provide co-deposited/co-treated HA discs, as discussed above. Particularly, the Hydrated HA discs were exposed to the first polymer (either GANTREZ® or PAA-G75) to establish a first layer, and subsequently treated with the second remaining polymer (either GANTREZ® or PAA-G75).

After incubation, the hydrated HA discs were washed with sterile DI water for 5 min and incubated in a bacterial suspension to simulate the bacterial biomass of the oral cavity. The bacterial suspension contained five oral bacterial/microbial species that were pre-labeled with hexidium iodide, namely, *Lactobacillus casei, Fusobacterium nucleatum, Streptococcus oxalis, Veillonella parvula*, and *Actinomyces viscosus*. The Hydrated HA discs were incubated in the bacterial suspension for 2 h at 37° C. and 90 rpm. After incubation, the bacteria that was not adhered to the samples were washed from the inoculated Hydrated HA discs with Phosphate Buffer Saline (PBS) three times at five minute intervals and 90 rpm. The totally adherence of the bacterial biomass was evaluated via confocal microscopy, analyzed using SYTO9 staining, and quantified via ImageJ. The quantified data of the bacterial adherence is illustrated in FIGS. 6 (a) and (b).

Figure 6A:
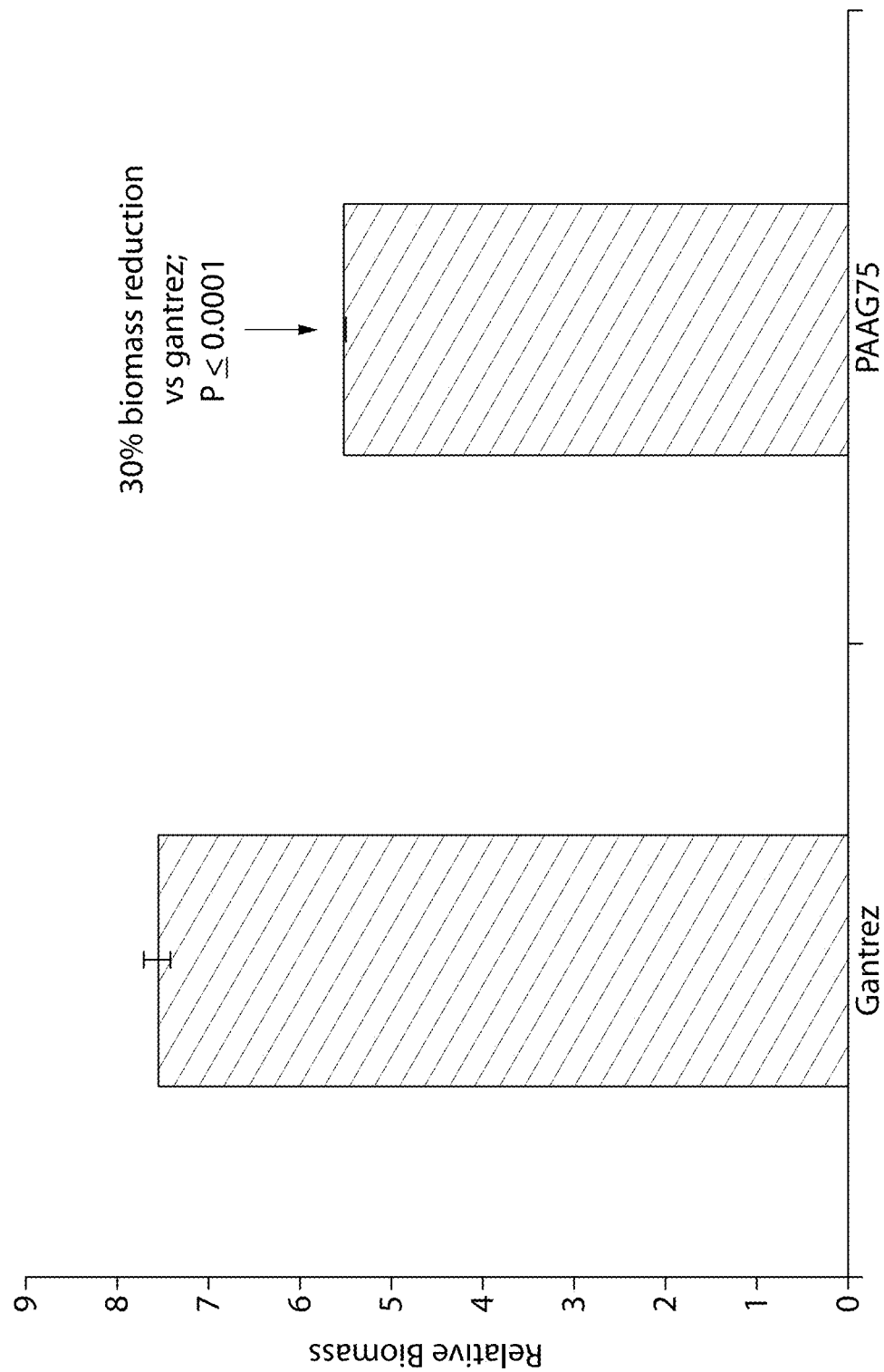
FIGS. 6 (a) and (b) illustrate plots of quantified data of the bacterial adherence studies of Example 9.

As is evident in FIG. 6(a), the PAA-G75 treated surfaces surprisingly and unexpectedly exhibited a statistically significant reduction of bacterial adherence as compared to the GANTREZ® treated surfaces. Particularly, the PAA-G75 treated surface exhibited a reduction of bacterial adherence of about 30% to about 40% as compared to the GANTREZ® treated surfaces.

Figure 6B:
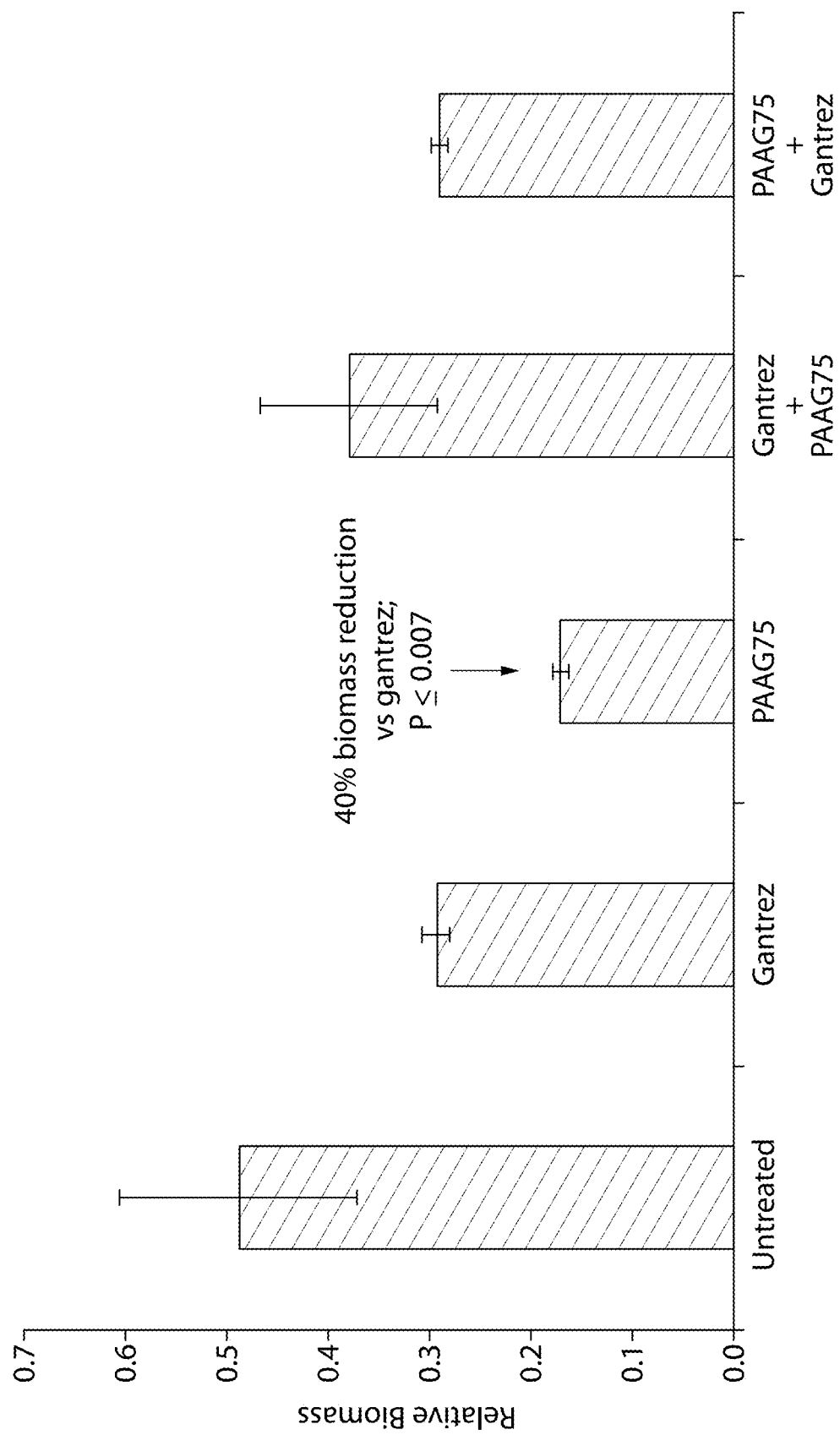

As illustrated in FIG. 6(b), the co-deposition of GANTREZ® and PAA-G75 on the treated discs (the GANTREZ®/PAA-G75 treated discs) surprisingly and unexpectedly exhibited a relatively decreased anti-attachment performance, or increased attachment of the bacteria, as compared to the PAA-G75 alone. The reduction in the anti-attachment performance was not affected by the order of deposition on the HA surface. For example, the relatively increased attachment as compared to the PAA-G75 alone was observed both when the GANTREZ® was deposited first and the PAA-G75 was deposited second, and when the PAA-G75 was deposited first and the GANTREZ® was deposited second. Accordingly, the increased attachment of the bacterial observed in the GANTREZ®/PAA-G75 treated discs was not dependent upon the order in which the polymers were adsorbed on the hydrated HA discs.

The data disclosed herein suggest the potential utility of cationic polymers having a poly-allylamine backbone and one or more guanidine functional groups, such as PAAG75, as an anti-biofilm molecule. The disclosure also supports the utility of the cationic polymer for inhibiting the early colonization that leads to biofilm accumulation, development, and formation on surfaces of the oral cavity. Accordingly, the disclosure supports the utility of the cationic polymer for oral care products, as discussed above. The disclosure further supports the utility of the cationic polymer for home care products, as discussed above, as the chemistry and biology of biofilm formation on various surfaces are similar.

Example 10

The antibacterial effect of the cationic polymer, PAA-G75, in comparison to GANTREZ® was evaluated via differential staining of bacteria. Particularly, antibacterial attachment performance of the cationic polymer, PAA-G75, against common primary colonizers of the oral cavity, namely, *Lactobacillus casei, Fusobacterium nucleatum, Streptococcus oralis, Veillonella parvula*, and *Actinomyces viscosus*, was evaluated. Additionally, the antibacterial effect of the cationic polymer was evaluated using vital staining that distinguished between living and dead/killed bacteria via damage to the cell wall and the quantification of total ATP in bacteria following contact with the cationic polymer.

To evaluate the cationic polymer, a bacterial suspension was incubated with a ~1% solution of either GANTREZ® or PAA-G75 at a pH of about 7 or 0.075% cetylpyridinium chloride (CPC) and incubated at 37° C. for 2 minutes. The 0.075% CPC was used as a positive control to illustrate the bactericidal effects of the polymer and its similarity with other antimicrobial molecules that target the bacterial cell wall. Following treatment, the bacteria were recovered and stained with Syto9 and propidium iodide to differentiate between intact and damage cells as well as the total ATP in the treated cells quantified. The results of the short interval kill treatment assay (SIKT) are summarized in Table 5.

TABLE 5

Short Interval Kill Treatment (SIKT) Assay*

| Polymer | % Killed (Live-Dead Stain) | % Viability Reduction (ATP) |
|---|---|---|
| 1% GANTREZ ® | −10.38% | 8.6% |
| 0.075% CPC | 98.85% | 95.67% |
| 1% PAAG75 | 41.58% | 94.8% |

*Assay was determined using LIVE/DEAD ® BacLight ™ Bacterial Viability Kit, commercially available from ThermoFisher Scientific of Waltham, MA, and BacTiter-Glo ™ Microbial Cell Viability Assay, commercially available from Promega Corp. of Madison, WI As is evident in Table 5, the PAA-G75 had a negative impact on the bacterial cell wall upon contact and exposure to the cationic polymer, which led to cell wall damage and bactericidal effects. This effect was observed following the vital staining of the bacteria with propidium iodide, which illustrated the permeability of the bacterial surface following contact with PAA-G75, which led to a 40% reduction in viable cells in comparison to GANTREZ® treated bacterial cells. This effect is similar to the mechanism of action for the 0.075% CPC, which has been shown to target the bacterial cell wall leading to bacteriolysis. In addition to the foregoing, the ATP quantification of the PAA-G75 treated bacteria indicated a surprisingly and unexpected ~95% reduction in viable cells post-CPC or -PAA-G75 treatment. The ATP quantification is summarized in Table 6.

TABLE 6

Bacterial Viability Quantification

| Polymer | Relative Luminescence Unite (RLU) | Std. Error | % Viability Reduction vs. Untreated |
|---|---|---|---|
| Untreated | 6850 | ±1055.0 | — |
| 1% GANTREZ ® | 7502 | ±772.16 | No Reduction |
| 1% PAAG75 | 364 | ±141.42 | 94.69 |
| 1% GANTREZ ® + 1% PAAG75$^a$ | 9516 | ±3286.63 | No Reduction |
| 1% PAAG75 + 1% GANTREZ ®$^b$ | 1156 | ±56.57 | 83.12 |

$^a$1% GANTREZ ® + 1% PAAG75 indicates that GANTREZ ® was first deposited followed by PAAG75
$^b$1% PAAG75 + 1% GANTREZ ® indicates that PAAG75 was first deposited followed by GANTREZ ®

Without being bound by theory, it is believed that contact between the cationic polymer and the cell wall and/or the accumulation of the cationic polymer within the extracellular bacterial surface of the cell wall destabilizes the cell wall, thereby leading to leakage and bacteriolysis.

Example 11

The contact effect of PAA-G75 was evaluated. To evaluate the contact effect of PAA-G75, HA discs were pre-coated or pre-treated with either GANTREZ® or PAA-G75, as discussed above. Additionally, the role of co-deposition on the antibacterial activity of PAA-G75 was determined via sequential coating of the HA discs with either (1) PAA-G75 followed by GANTREZ®, or (2) GANTREZ® followed by PAA-G75. The treated discs were exposed to a suspension of bacteria (Optical Density=0.2) for two hours and a total cell viability was assessed by ATP quantification. The results are summarized in Table 6.

Consistent with the SIKT assays, contact with the PAA-G75 treated HA discs showed a reduction in cell viability in comparison to the GANTREZ® treated HA discs and the untreated HA discs. In addition to the foregoing, it was surprisingly and unexpectedly discovered that the antibacterial activity of PAA-G75 was at least partially dependent upon or determined by the sequence of polymer deposition.

For example, the antibacterial activity of PAA-G75 was relatively lower when a subsequent layer of GANTREZ® was adsorbed as a second layer. Without being bound by theory, it is believed that the electrostatic cross-linking interaction of the GANTREZ® anionic polymer with PAA-G75 cationic polymer could induce to disperse the PAA-G75 polymer, which could be moved to the outer layer and restored the antibacterial performance, but some of the GANTREZ® anionic polymer atop the PAA-G75 cationic polymer could partially impede the PAA-G75 from contacting the surface of the bacterial cell wall; and thus, the antibacterial activity of PAA-G75 was slightly mitigated (% viability reduction=83.12) but the high molecular weight GANTREZ® polymer could act to stabilize the PAAG75 in the coating. According to morphological studies of the mixed layer, in the HA discs treated firstly with the GANTREZ® and subsequently with the PAA-G75 polymer, such that the PAA-G75 cationic polymer could be non-homogenously and irregularly adsorbed on the GANTREZ® anionic polymer layer resulting in a patchy surface, which showed high Std. Error (±3286.63) as well as high Relative Luminescence Unite. These results illustrated the bactericidal activity of PAA-G75.

Example 12

Figure 7:
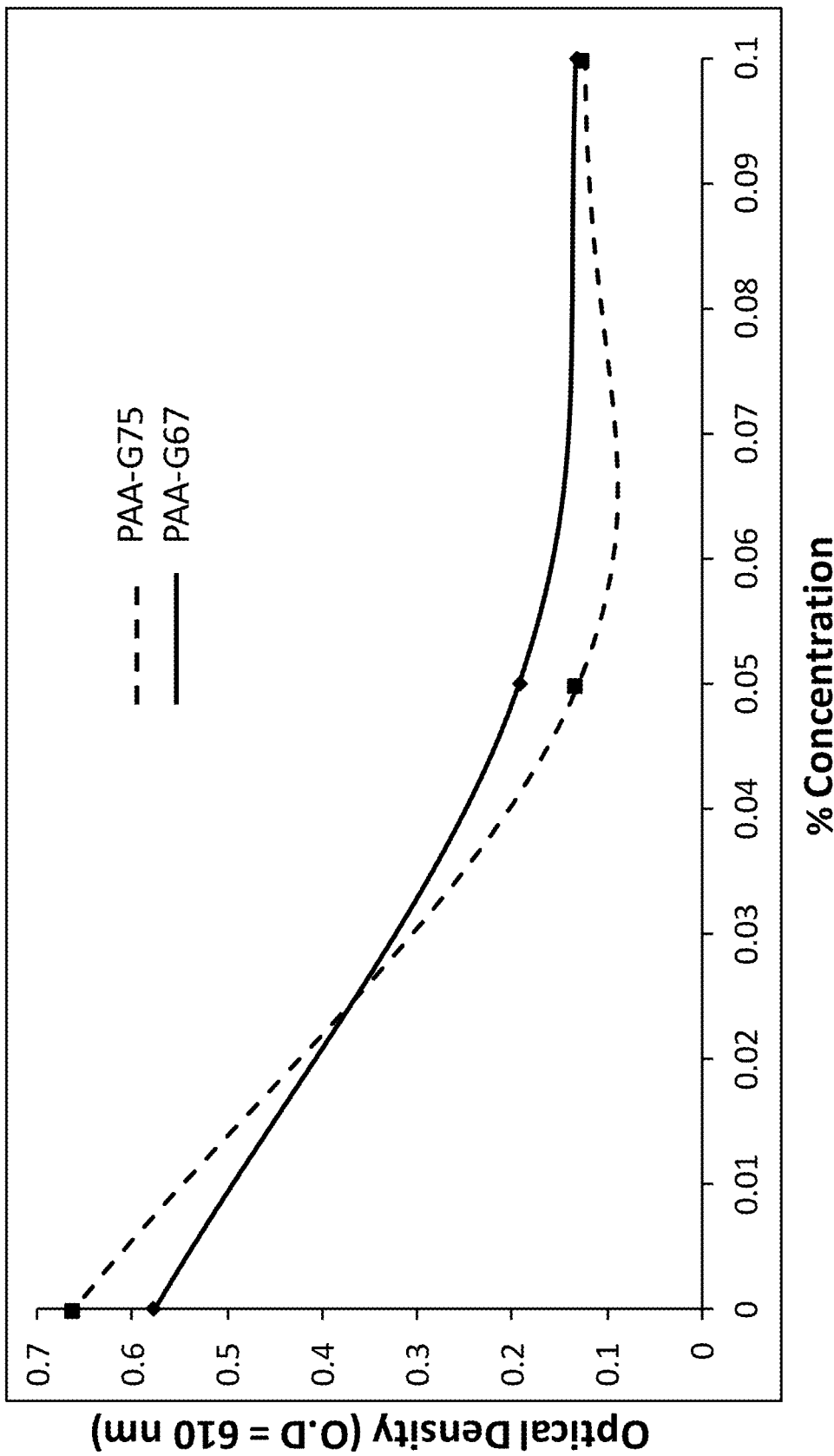
FIG. 7 illustrates a plot of the minimum inhibitor concentration (MIC) analysis of Example 12.

Minimum inhibitor concentration (MIC) analysis was evaluated to identify the compositional impact of guanidine on *E. coli*. To evaluate the MIC, *E. coli* was suspended at a starting optical density (O.D) of about 0.2 in DMEM containing varying concentrations of PAA-G75 (about 75% guanidine functionalization) and PAA-G67 (about 67% guanidine functionalization). The bacteria was incubated with the polymers at 37° C. overnight with the O.D. of the bacterial culture identified hourly for a total of 16 hours. The results of the assay are illustrated in FIG. 7 and identify similar IC50 for both PAA-G75 and PAA-G67 (<0.05%). The results suggest the composition requirements necessary to maintain the bactericidal activity of the polymer has been achieved. Particularly, based on structure function studies, a minimum composition of 67% guanidine is necessary to deliver an antibacterial effect in the currently described polymer system.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:

1. An antimicrobial composition, comprising a cationic polymer having a poly-allylamine backbone, wherein the poly-allylamine backbone is about 75% functionalized with a guanidine functional group; and wherein the cationic polymer having the poly-allyalamine backbone reduces oral bacteria adherence to hydroxyapatite surfaces 30-40% more than an anionic polymer comprising polyvinylmethylether/maleic anhydride (PVM/MA) copolymer.

2. An oral care composition, comprising:
the antimicrobial composition of claim 1; and
an orally acceptable vehicle.

3. The oral care composition of claim 2, wherein the antimicrobial composition does not comprise an anionic polymer.

4. The oral care composition of claim 2, wherein the oral care composition is at least one of a mouthwash and a toothpaste.

5. A cleansing composition, comprising:
a soap; and
the antimicrobial composition of claim 1.

6. The antimicrobial composition of claim 1, wherein the antimicrobial composition further comprises a substrate.

* * * * *